(12) United States Patent
Suzuki et al.

(10) Patent No.: US 10,842,458 B2
(45) Date of Patent: Nov. 24, 2020

(54) IMAGE PROCESSING APPARATUS, RADIOGRAPHIC IMAGING SYSTEM, RADIOGRAPHIC LENGTHY IMAGE IMAGING METHOD AND RECORDING MEDIUM

(71) Applicant: Konica Minolta, Inc., Tokyo (JP)

(72) Inventors: Masaki Suzuki, Tokyo (JP); Masahiro Kuwata, Tokyo (JP); Atsushi Yamanishi, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 16/231,775

(22) Filed: Dec. 24, 2018

(65) Prior Publication Data
US 2019/0223818 A1    Jul. 25, 2019

(30) Foreign Application Priority Data
Jan. 24, 2018   (JP) ................. 2018-009703

(51) Int. Cl.
*A61B 6/00*   (2006.01)
*G06T 7/62*   (2017.01)
*G06T 3/40*   (2006.01)

(52) U.S. Cl.
CPC .......... *A61B 6/5205* (2013.01); *A61B 6/4266* (2013.01); *A61B 6/5241* (2013.01); *G06T 3/4007* (2013.01); *G06T 3/4023* (2013.01); *G06T 7/62* (2017.01); *G06T 2207/10116* (2013.01); *G06T 2207/20221* (2013.01)

(58) Field of Classification Search
CPC .... A61B 6/4266; A61B 6/5205; A61B 6/5241
See application file for complete search history.

(56) References Cited

U.S. PATENT DOCUMENTS

| 2016/0074001 | A1* | 3/2016 | Matsushita | ............ A61B 6/566 378/62 |
| 2016/0287195 | A1* | 10/2016 | Tagawa | .................. A61B 6/465 |

FOREIGN PATENT DOCUMENTS

| JP | 2013154146 A | 8/2013 |
| JP | 2016187380 A | 11/2016 |

* cited by examiner

*Primary Examiner* — Dani Fox
(74) *Attorney, Agent, or Firm* — Lucas & Mercanti, LLP

(57) ABSTRACT

An image processing apparatus 3 is provided with a hardware processor that acquires first image data and second image data which is different from the first image data from among a plurality of pieces of image data, detects a width in a direction orthogonal to a direction in which a first image based on the acquired first image data and a second image based on the second image data are arranged side by side, corrects, when the detected width of the first image is different from the width of the second image, at least one piece of image data of the first image data and the second image data so that the widths of both pieces of image data come closer to each other, and combines a plurality of pieces of image data including the corrected image data to thereby generate one piece of lengthy image data.

16 Claims, 18 Drawing Sheets

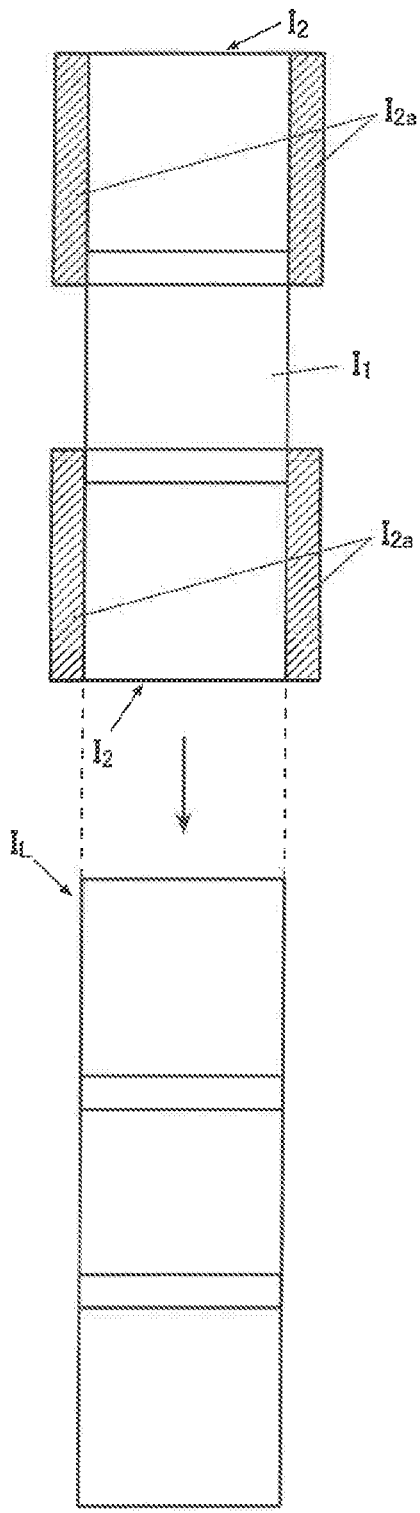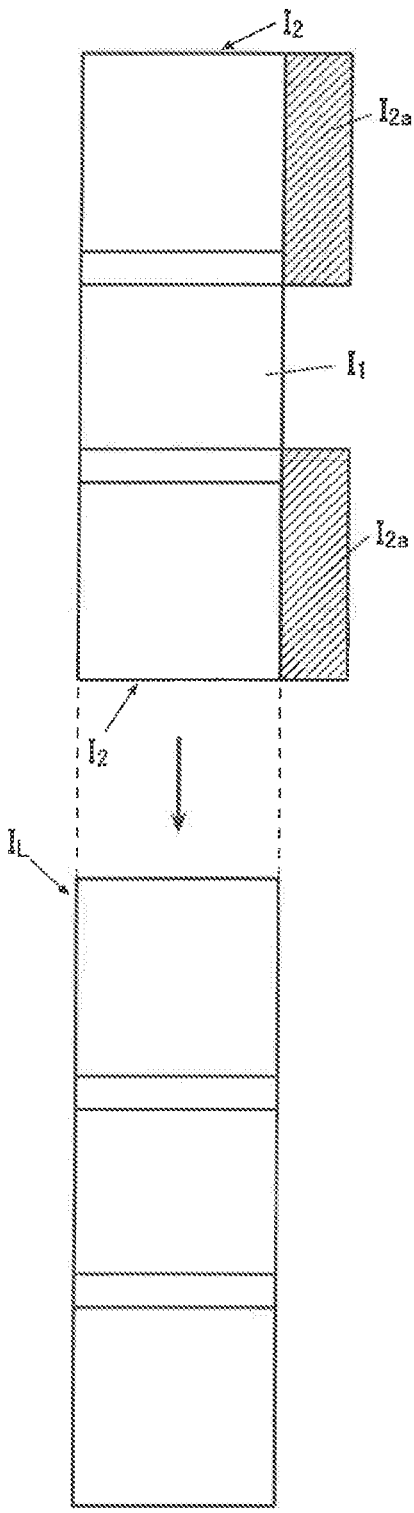

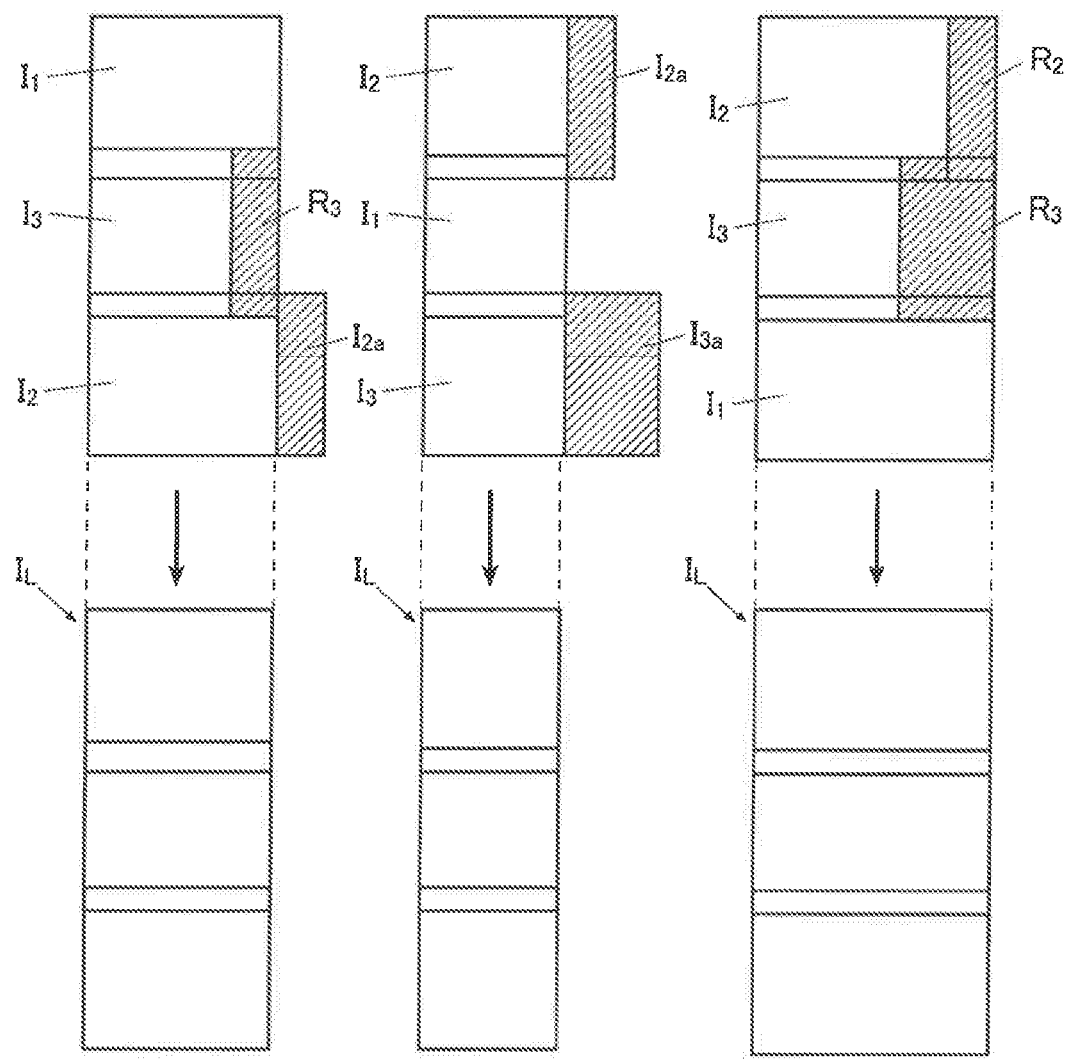

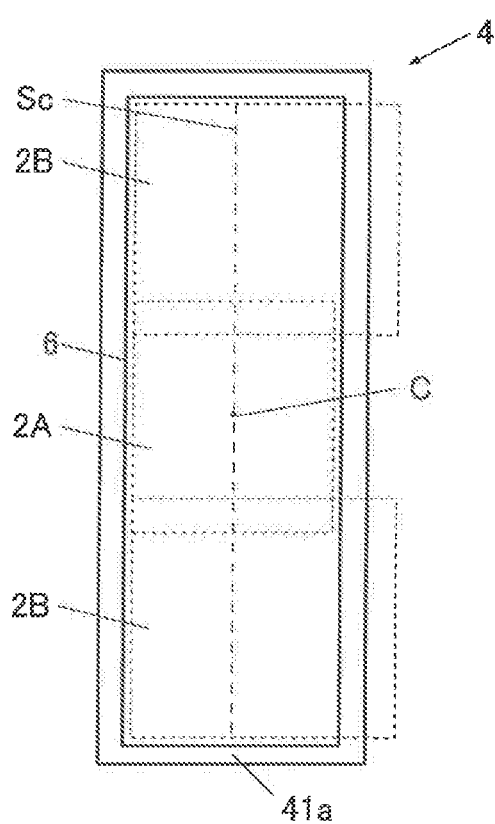

IMAGE PROCESSING APPARATUS, RADIOGRAPHIC IMAGING SYSTEM, RADIOGRAPHIC LENGTHY IMAGE IMAGING METHOD AND RECORDING MEDIUM

BACKGROUND

Technical Field

The present invention relates to an image processing apparatus, a radiographic imaging system, a radiographic lengthy image imaging method and a recording medium.

Description of the Related Art

One of radiographic image imaging methods is called "lengthy imaging." Lengthy imaging targets a region over a wide range such as the whole spine and the whole lower limb, and repeatedly takes images (radiation exposures) of the imaging target region while moving a radiographic imaging apparatus or, as described, for example, in Japanese Patent Laid-Open No. 2016-187380, this is a imaging method in which a plurality of radiographic imaging apparatuses are arranged along a longitudinal direction of an imaging target region of a subject, a plurality of images obtained by single imaging are combined, and images in greater size than normal radiographic images (hereinafter referred to as "lengthy images") are thereby generated. Lengthy imaging using a plurality of radiographic imaging apparatuses makes it possible to prevent imaging from failing because of the subject's bodily movement in the middle of imaging or reduce an exposure quantity of the subject.

Japanese Patent Laid-Open No. 2013-154146 describes an example of the technique for combining a plurality of images. More specifically, this technique identifies overlapping regions where neighboring images overlap for image data outputted from each radiographic imaging apparatus, detects a position of an end portion of an imaging target region from a profile in a width direction of the overlapping region and causes the overlapping regions to superimpose one image on another so that the positions of the imaging target regions obtained from both neighboring images match.

However, since radiographic imaging apparatuses are expensive, there may be some institutions using such radiographic imaging apparatuses which may not be able to afford to purchase a plurality of the same radiographic imaging apparatuses at a time. Such institutions purchase the plurality of the same radiographic imaging apparatuses in several installments, and so there may be cases where apparatuses of the same model as those in their possession cease to be circulated in the middle of use or only smaller apparatuses than those in their possession can be purchased, ending up possessing the plurality of radiographic imaging apparatuses of different sizes.

Even when a plurality of radiographic imaging apparatuses are purchased at a time, apparatuses in different sizes may be intentionally purchased in consideration of use in a variety of scenes in the future.

However, the technique described in Japanese Patent Laid-Open No. 2013-154146 is a technique presupposing that image data pieces to be combined are image data, all of which have the same size, and if the apparatuses are used to combine image data pieces of different sizes, errors may occur in the middle of processing, making it impossible to obtain desired lengthy images.

Furthermore, even if a combining technique applicable to other image data of different sizes exists, processing may take much time or images may become non-rectangular, bad-looking lengthy images.

SUMMARY

It is an object of the present invention to facilitate combining of a plurality of pieces of image data when combining the plurality of pieces of image data into one lengthy piece of image data even when the pieces of image data have different sizes.

To achieve at least one of the abovementioned objects, according to a first aspect of the present invention, an image processing apparatus reflecting one aspect of the present invention comprises a hardware processor which acquires first image data and second image data which is different from the first image data from among a plurality of pieces of image data generated by a plurality of radiographic imaging apparatuses disposed so as to form a line along an imaging target region of a subject and respectively generating image data of radiographic images by receiving radiation via the imaging target region, detects a width in a direction orthogonal to a direction in which a first image based on the first image data acquired and a second image based on the second image data form a line, corrects, when the width of the first image detected is different from the width of the second image, at least one piece of image data of the first image data and the second image data so that the widths of both pieces of image data come closer to each other, and combines a plurality of pieces of image data including the image data corrected to thereby generate one piece of lengthy image data.

According to a second aspect of the present invention, a radiographic lengthy image imaging method reflecting one aspect of the present invention comprises arranging a plurality of radiographic imaging apparatuses which generate image data of radiographic images by receiving radiation so as to form a line along an imaging target region of a subject, capturing radiographic images of the subject, extracting first image data and second image data which is different from the first image data from among the plurality of pieces of image data generated by the radiographic imaging apparatuses, measuring a width in a direction orthogonal to a direction in which a first image based on the extracted first image data and a second image based on the second image data are arranged side by side, correcting, when the measured width of the first image is different from the width of the second image, at least one piece of image data of the first image data and the second image data so that the widths of both pieces of image data come closer to each other, and combining a plurality of radiographic images including the corrected image data to thereby generate one piece of lengthy image data.

According to a third aspect of the present invention, a non-transitory computer-readable recording medium reflecting one aspect of the present invention comprises storing a program for causing a computer to perform acquiring first image data and second image data which is different from the first image data from among a plurality of pieces of image data generated by a plurality of radiographic imaging apparatuses disposed so as to form a line along an imaging target region of a subject and generating image data of radiographic images by receiving radiation via the imaging target region, detecting a width in a direction orthogonal to a direction in which a first image based on the acquired first image data and a second image based on the second image data are arranged side by side, correcting, when the detected width of the first image is different from the width of the second image, at least one piece of image data of the first image data and the second image data so that the widths of both pieces of image data come closer to each other, and combining a plurality of pieces of image data including the corrected image data to thereby generate one piece of lengthy image data.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

FIG. 11A is a conceptual diagram illustrating an image data correction method;

FIG. 11B is a conceptual diagram illustrating an image data correction method;

FIG. 13A is a conceptual diagram illustrating an image data correction method;

FIG. 13B is a conceptual diagram illustrating an image data correction method;

FIG. 13C is a conceptual diagram illustrating an image data correction method;

FIG. 14 is a front view illustrating a radiographic imaging apparatus, a holder and a grid provided for a radiographic imaging system according to example 1 of the embodiment;

BRIEF DESCRIPTION OF EMBODIMENTS

Hereinafter, one or more embodiments of the present invention will be described with reference to the drawings. However, the scope of the invention is not limited to the disclosed embodiments.

[Configuration of Radiographic Imaging System]

Figure 1:
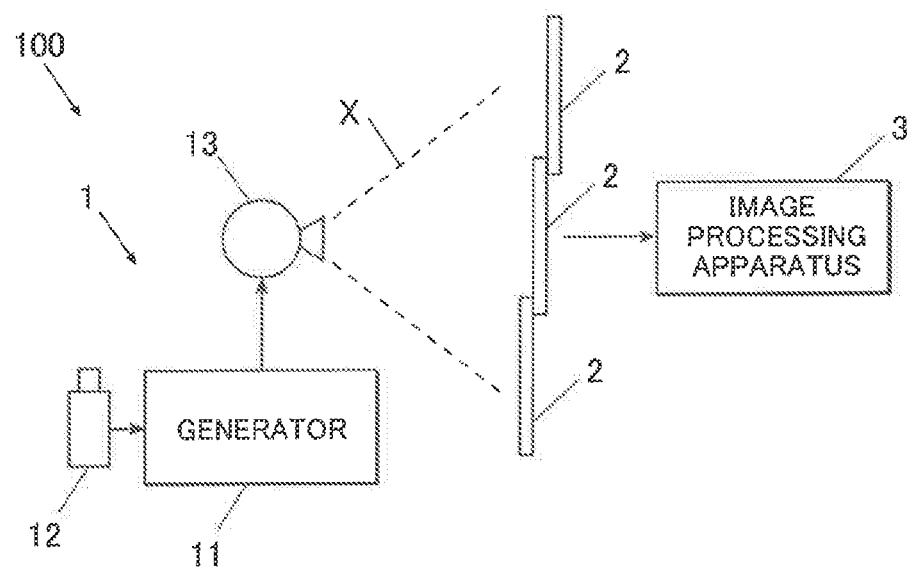
FIG. 1 is a block diagram illustrating a schematic configuration of a radiographic imaging system according to an embodiment of the present invention.

A schematic configuration of a radiographic imaging system according to the present embodiment will be described first. FIG. 1 is a block diagram illustrating a configuration of a radiographic imaging system 100 of the present embodiment.

The radiographic imaging system 100 of the present embodiment is constructed of a radiation exposure apparatus 1, a plurality of radiographic imaging apparatuses (hereinafter referred to as "imaging apparatus 2") and an image processing apparatus 3 or the like as shown in FIG. 1.

Furthermore, the radiographic imaging system 100 can be connected to a radiology information system (RIS) (not shown), an image storage communication system (picture archiving and communication system: PACS) or the like.

The radiation exposure apparatus 1 is intended to generate radiation and is provided with a generator 11, an exposure switch 12 and a radiation source 13 or the like.

The generator 11 is configured to be able to apply a voltage corresponding to predetermined radiation exposure conditions (tube voltage, tube current, irradiation time (mAs value) or the like) to the radiation source 13 based on operation on the exposure switch 12.

The radiation source 13 (tube bulb) includes a rotating anode and a filament (which are not shown) or the like. When a voltage is applied from the generator 11, the filament radiates an electron beam corresponding to the applied voltage onto the rotating anode so that the rotating anode generates radiation X (X-rays or the like) with a dose corresponding to the intensity of the electron beam.

Note that although FIG. 1 illustrates the exposure switch 12 connected to the generator 11, the exposure switch 12 may also be provided for another apparatus (e.g., operation console (not shown)) connected to the generator 11.

Furthermore, the radiation exposure apparatus 1 may be installed in an imaging room or configured to be movable by being assembled into a mobile visiting car or the like.

The plurality of imaging apparatuses 2 are connected to the image processing apparatus 3 in a communicable manner by a cable or radio.

Each imaging apparatus 2 is enabled to generate image data of radiographic images corresponding to radiation received from the outside and transmit the image data to the image processing apparatus 3.

Note that details of the imaging apparatus 2 will be described later.

The image processing apparatus 3 is constructed of a PC, a portable terminal or a dedicated apparatus and connected to the imaging apparatus 2 or the like in a communicable manner by a cable or radio.

The image processing apparatus 3 is enabled to receive image data from the plurality of imaging apparatuses 2 by a cable or radio, combine the image data and generate lengthy image $I_L$.

Note that a console for setting various imaging conditions of the radiation exposure apparatus 1 and the imaging apparatus 2 and a dedicated analysis apparatus for applying predetermined image processing to image data may be connected to the radiographic imaging system 100 to be used as the image processing apparatus 3.

[Configuration of Radiographic Imaging Apparatus]

Figure 2:
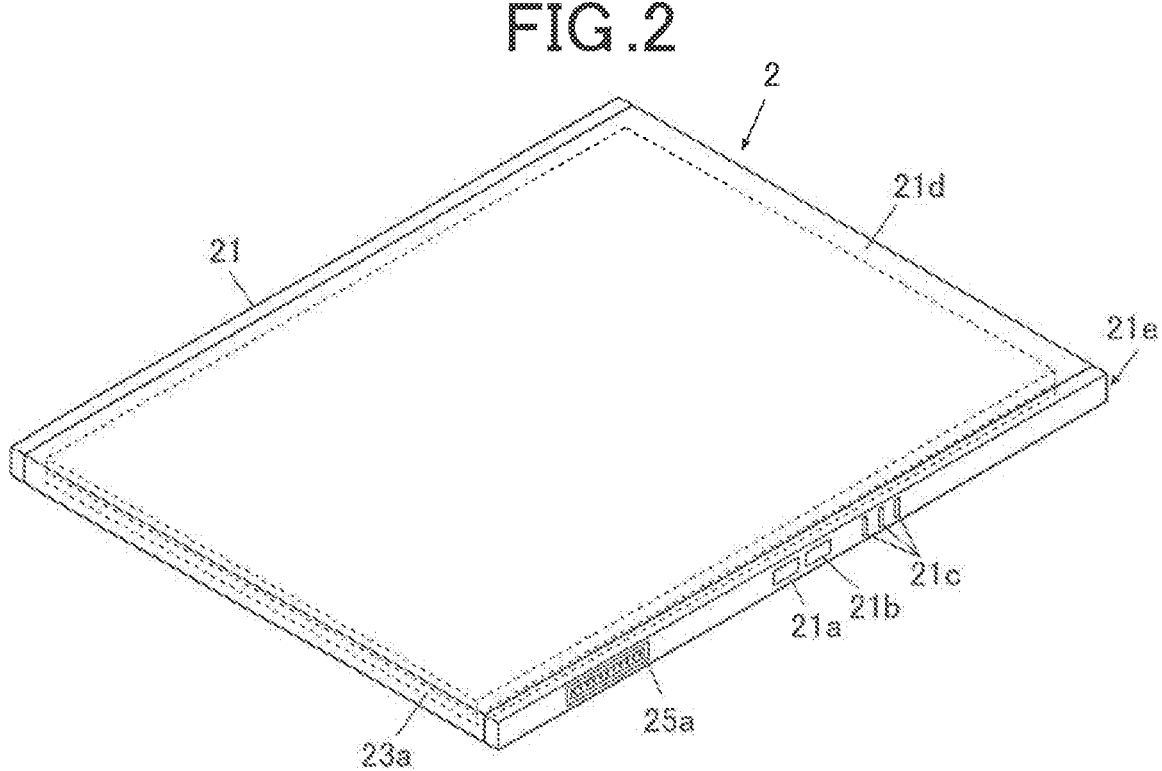
FIG. 2 is a perspective view showing an appearance of a radiographic imaging apparatus provided for the radiographic imaging system in FIG. 1.

Next, details of the imaging apparatus 2 constituting the radiographic imaging system 100 will be described. FIG. 2 is a perspective view showing an appearance of the imaging apparatus 2, FIG. 3 is a block diagram illustrating an electrical configuration of the imaging apparatus 2 and FIG. 4 is a plan view illustrating an example of a sensor substrate 23a provided for the imaging apparatus 2.

Figure 3:
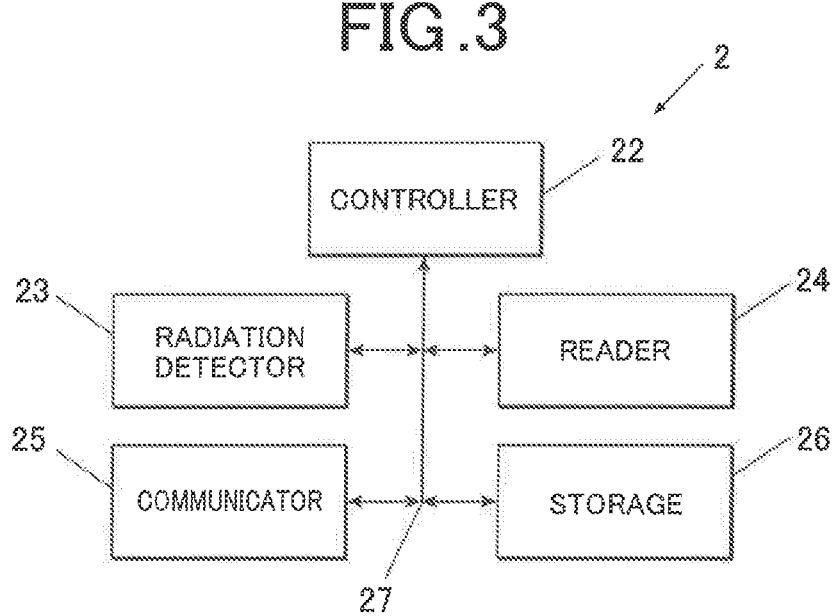
FIG. 3 is a block diagram illustrating an electrical configuration of the radiographic imaging apparatus in FIG. 2.
Figure 4:
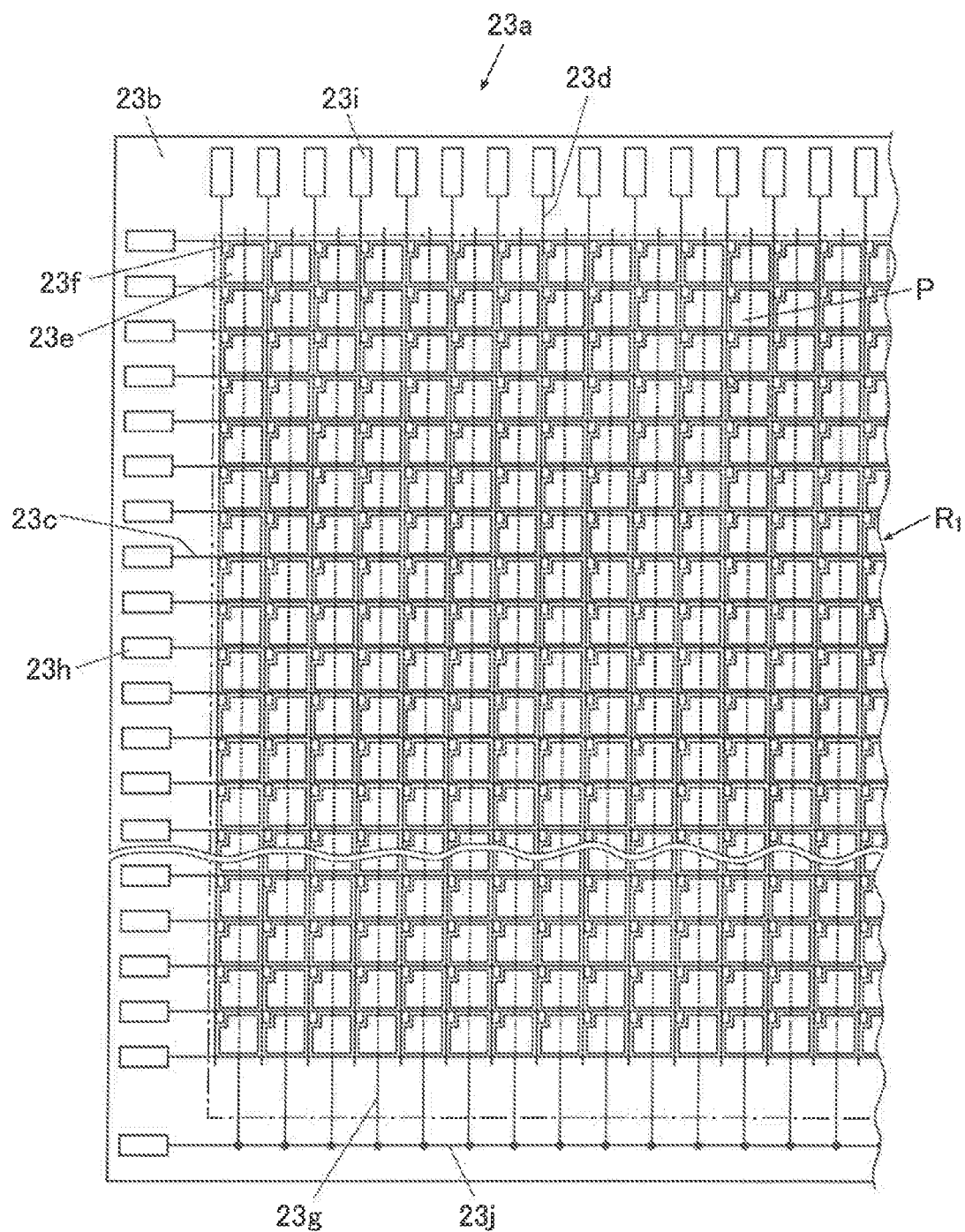
FIG. 4 is a plan view illustrating part of a radiation detector provided for the radiographic imaging apparatus in FIG. 2.

As shown in FIG. 2, the imaging apparatus 2 is provided with a casing 21 and the casing 21 is internally provided with a controller 22, a radiation detector 23, a reader 24, a communicator 25, a storage 26 and a bus 27 that connects the respective parts 22 to 26 shown in FIG. 3.

Electric power is supplied from a built-in battery (not shown) or an external power supply to the respective parts 22 to 26 of the imaging apparatus 2.

One of a plurality of planes of the casing 21 (e.g., the broadest plane) constitutes a radiation incident plane 21d.

As shown in FIG. 2, a power switch 21a, an operation switch 21b, an indicator 21c, the connector 25a or the like are provided on the surface (e.g., side face) of the casing 21. The surface of the casing 21 on which the power switch 21a or the like is provided is referred to as an "IF (interface) surface 21e."

The controller 22 is configured to integrally control operations of the respective parts of the imaging apparatus 2 through a CPU (central processing unit), a RAM (random access memory) or the like. More specifically, triggered by turning on of the power switch, reception of a predetermined control signal from an external apparatus, reception of radiation from the radiation exposure apparatus 1 or the like, the controller 22 reads various processing programs stored in the storage 26, develops the programs on the RAM and executes various processes according to the processing programs.

The radiation detector 23 needs only to include a sensor substrate 23a (see FIG. 4) with a plurality of two-dimensionally arranged pixels including radiation detection elements that directly or indirectly generate a quantity of charge corresponding to a dose of radiation and switch elements provided between each radiation detection element and wiring and capable of switching between an ON state in which current can flow between the radiation detection element and the wiring and an OFF state in which current cannot flow between the radiation detection element and the wiring, or a conventionally known radiation detector can be used.

That is, the imaging apparatus 2 may be of a so-called indirect type provided with a scintillator, which detects light emitted from the scintillator upon receiving radiation or may be of a so-called direct type, which directly detects radiation without any scintillator.

The reader 24 may be configured to read charge quantities respectively stored in the plurality of radiation detection elements as signal values and enabled to generate image data based on the respective signal values, and a conventionally known reader can be used.

The communicator 25 is constructed of a network interface or the like and transmits/receives data to/from an external apparatus connected via a communication network such as a LAN (local area network), a WAN (wide area network) or the Internet.

The communicator 25 is also provided with the connector 25a (see FIG. 2) for wired communication.

The storage 26 is constructed of an HDD (hard disk drive), a semiconductor memory or the like and stores various processing programs including a program for executing various types of image processing, parameters and files necessary to execute these programs.

The sensor substrate 23a included in the aforementioned radiation detector 23 is housed in the casing 21 as shown in FIG. 2 so as to extend in parallel to the radiation incident plane 21d.

Furthermore, the sensor substrate 23a is constructed of a substrate 23b, a plurality of scan lines 23c, a plurality of signal lines 23d, a plurality of radiation detection elements 23e, a plurality of TFTs 23f, a plurality of bias lines 23g or the like as shown, for example, in FIG. 4. A rectangular region enclosed by the neighboring scan lines 23c and the neighboring signal lines 23d constitutes one pixel P.

Furthermore, a plurality of terminals 23h for connecting the respective scan lines 23c to a gate driver (not shown), a plurality of terminals 23i for connecting the respective signal lines 23d to a reading circuit (not shown) and a connection line 23j connecting respective bias lines 23g or the like are formed at peripheral edges of the substrate 23b.

For this reason, the region where the pixels P are arranged is slightly smaller than the substrate 23b as shown in FIG. 4. Hereinafter, the region of the sensor substrate 23a where the plurality of pixels P are arranged (region excluding the peripheral edges where no pixel R exists) is referred to as an "effective imaging region R1."

Figure 5A:
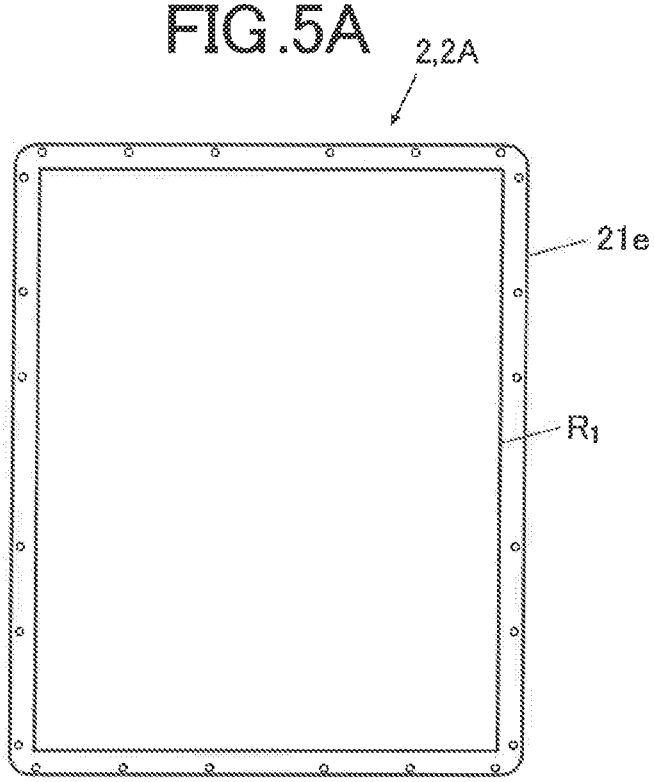
FIG. 5A is a plan view illustrating an example of the radiographic imaging apparatus in FIG. 2.
Figure 5B:
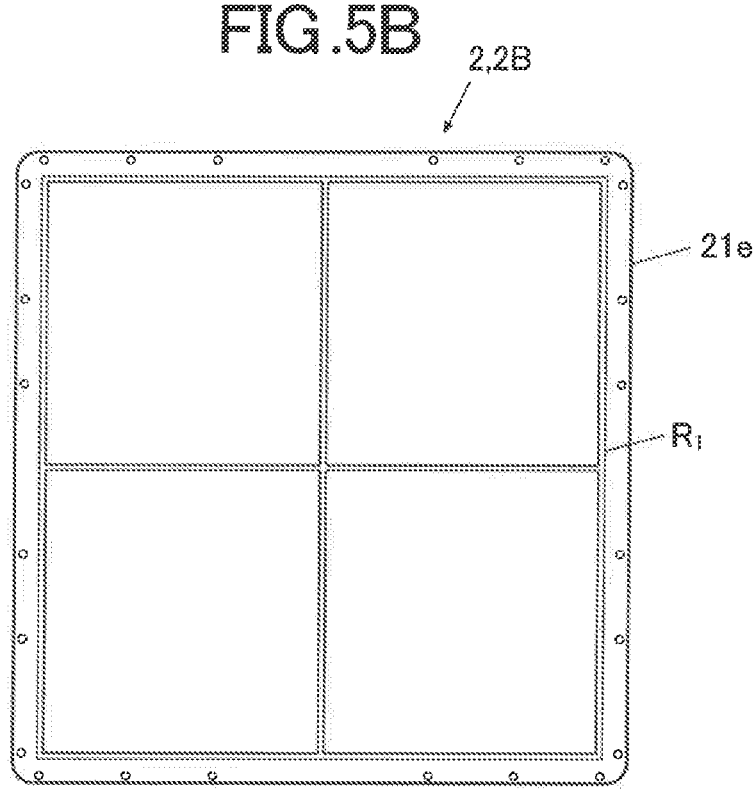
FIG. 5B is a plan view illustrating another example of the radiographic imaging apparatus in FIG. 2.

Note that the imaging apparatus 2 can be configured into various sizes by changing the sizes of the casing 21 and the sensor substrate 23a or the number of pixels P arranged or the like. More specifically, as shown in FIG. 5A, the length (hereinafter, referred to as a "width") in the direction orthogonal to the longitudinal direction of an IF surface 21e (hereinafter, referred to as a "height") and the thickness direction of the imaging apparatus 2 may be shorter or the length in the width direction is larger compared to the height as shown in FIG. 5B.

Hereinafter, when necessary, an imaging apparatus having a relatively small width will be represented by an "imaging apparatus 2A" and an imaging apparatus having a relatively large width will be represented by an "imaging apparatus 2B."

[Holder]

Figure 6A:
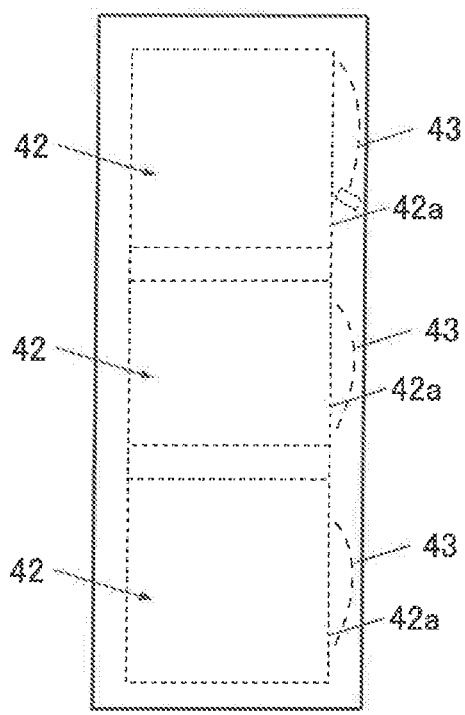
FIG. 6A is a front view illustrating an example of a holder provided for the radiographic imaging apparatus in FIG. 2.
Figure 7A:
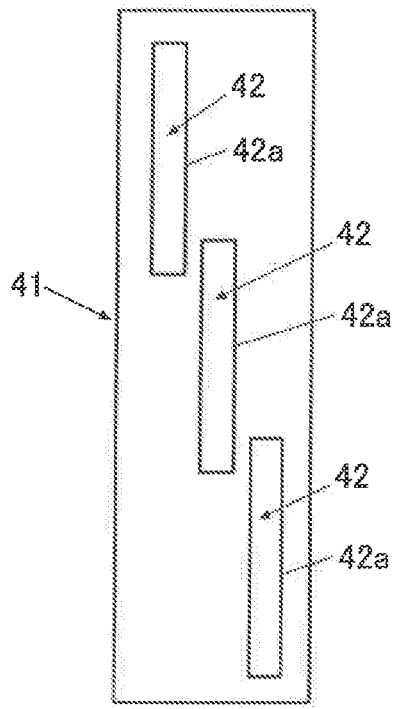
FIG. 7A is a side view illustrating another example of the holder provided for the radiographic imaging apparatus in FIG. 2.
Figure 7B:
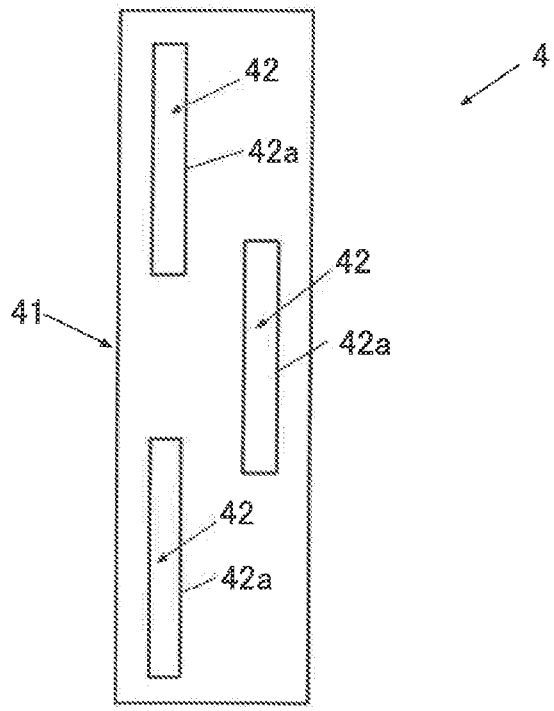
FIG. 7B is a side view illustrating a further example of the holder provided for the radiographic imaging apparatus in FIG. 2.
Figure 8A:
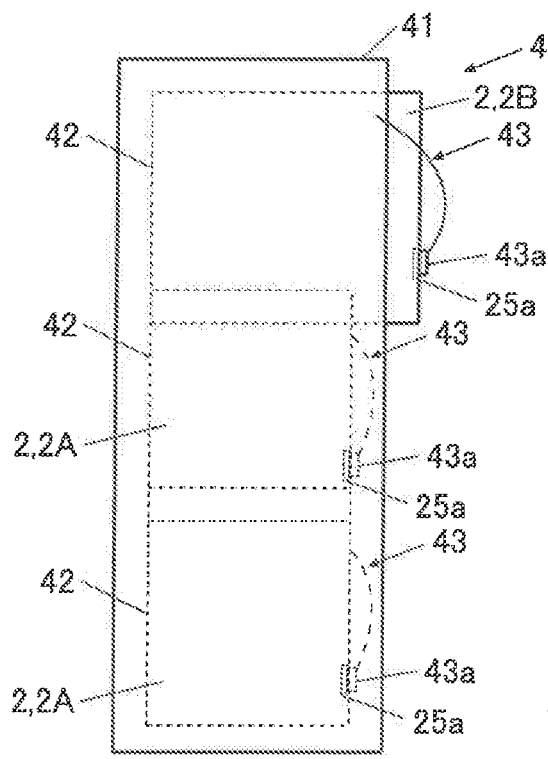
FIG. 8A is a schematic diagram illustrating an example of a method of loading the radiographic imaging apparatus into the holder in FIG. 6A, FIG. 7A or FIG. 7B.
Figure 8B:
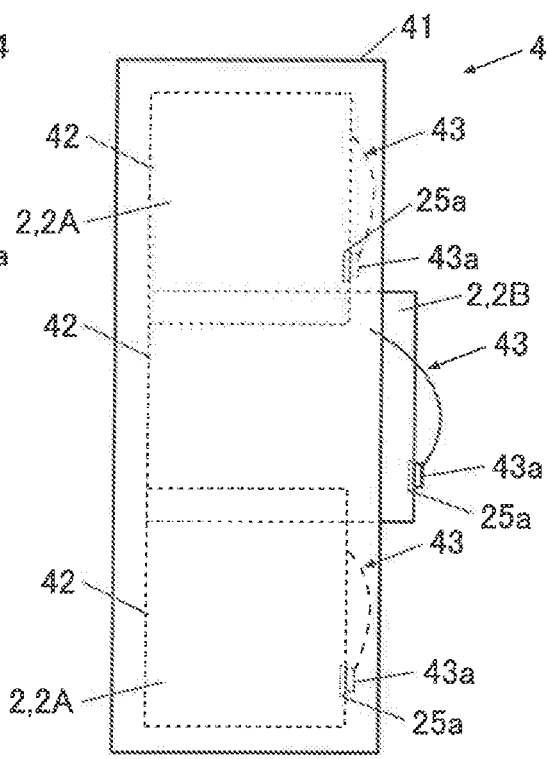
FIG. 8B is a schematic diagram illustrating another example of the method of loading the radiographic imaging apparatus into the holder in FIG. 6A, FIG. 7A or FIG. 7B.
Figure 8C:
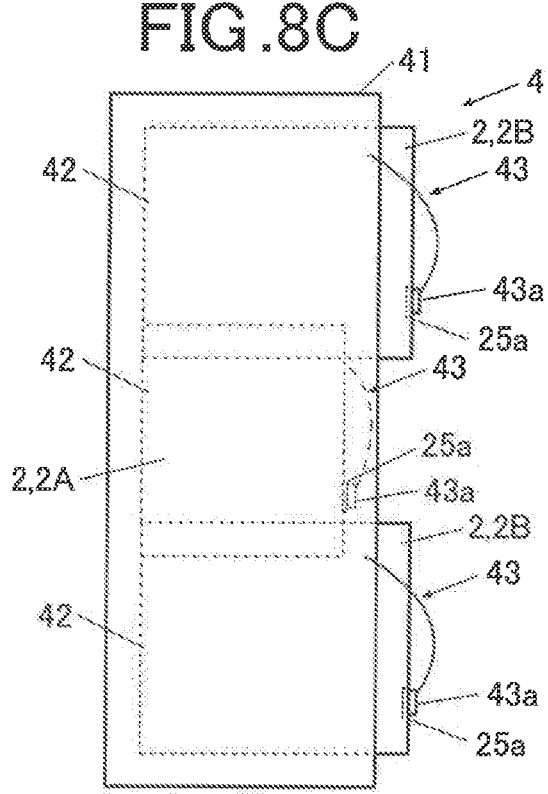
FIG. 8C is a schematic diagram illustrating a further example of the method of loading the radiographic imaging apparatus into the holder in FIG. 6A, FIG. 7A or FIG. 7B.

Next, a holder 4 into which the imaging apparatus 2 is loaded will be described. FIG. 6A is a front view illustrating an example of the holder 4, FIG. 6B is a side view illustrating an example of the holder 4, FIG. 7A and FIG. 7B are side views illustrating other examples of the holder 4, and FIG. 8A, FIG. 8B and FIG. 8C are schematic diagrams illustrating examples of loading the imaging apparatus 2 into the holder 4.

The holder 4 is intended to fix relative positions of the plurality of imaging apparatuses 2 and is constructed of a body 41, loaders 42 in a plurality of stages and a plurality of cables 43 or the like.

The body 41 is formed into a substantially rectangular parallelepiped shape and the front thereof constitutes a radiation incident plane 41a.

Figure 6B:
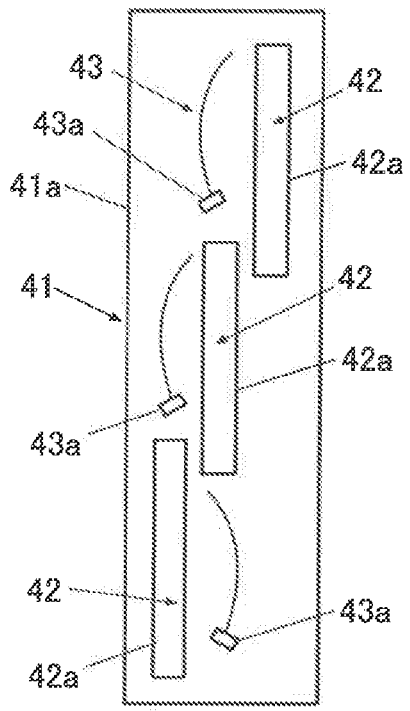
FIG. 6B is a side view of the holder shown in FIG. 6A.

The plurality of loaders 42 are spaces that can be loaded with the imaging apparatus 2 and provided in the body 41 so as to form a line along the longitudinal direction of the body 41 as shown in FIG. 6A and FIG. 6B. Note that FIG. 6A and FIG. 6B illustrate an example where the number of loaders 42 is three, but the number of loaders 42 may be two or four or more.

In a side view, the positions of the respective loaders 42 in the front-back direction are slightly shifted from one another as shown in FIG. 6B and when seen from a direction orthogonal to the radiation incident plane 41a, a top end portion of the lower loader 42 overlaps a lower end portion of the upper loader 42. An overlapping width is longer than a distance between the side face of the casing 21 of the imaging apparatus 2 and the effective imaging region R1.

One side face of each loader 42 constitutes a loading port 42a through which the imaging apparatus 2 is inserted.

The length in the width direction of the imaging apparatus 2 to be loaded in each loader 42 (hereinafter referred to as a "width of the loader 42") is shorter than the longest width of a plurality of types of the loadable imaging apparatuses 2A and 2B. It is particularly preferable that the width of the loader 42 be equal to the shortest width of the plurality of types of the loadable imaging apparatuses 2A and 2B.

Note that FIG. 6B illustrates the upper loader 42 positioned behind the lower loader 42, but the respective loaders 42 may be arranged as shown, for example, in FIG. 7A such that the lower loader 42 is positioned behind the upper loader.

Although FIG. 6B and FIG. 7A illustrate a case where the positions in the front-back direction of all the loaders 42 are different, the loaders 42 may be disposed such that the positions in the front-back direction of a plurality of loaders 42 (2; top and bottom) which are fewer than the total number (here 3) are the same as shown, for example, in FIG. 7B.

As shown in FIG. 6B, the plurality of cables 43 are led out from the vicinity of each loading port 42a of the body 41.

A distal end portion of each cable 43 constitutes a plug 43a which can be inserted into the connector 25a of the imaging apparatus 2.

Note that although not illustrated, an intermediate portion of each cable is passed through the body 41, a proximal end portion of each cable 43 is led out from the body 41 and connected to the image processing apparatus 3.

Note that when the holder 4 is used for standing imaging, the holder 4 can be mounted on a support 5 (see FIG. 21A) and used.

By loading each loader 42 of the holder 4 configured in this way with the imaging apparatus 2, the plurality of imaging apparatuses 2 are arranged in a line, making it possible to perform lengthy imaging.

As described above, since the overlapping width of the upper and lower loaders 42 is longer than the distance between the side face of the casing 21 of the imaging apparatus 2 and the effective imaging region R1, each imaging apparatus 2 loaded into the holder 4 partially overlaps the effective imaging region R1 when seen from the direction orthogonal to the radiation incident plane 41a.

Note that the holder 4 can be loaded with the aforementioned imaging apparatuses 2A and 2B of different sizes simultaneously. More specifically, as shown in FIG. 8A and FIG. 8B, a certain one loader 42 may be loaded with the imaging apparatus 2B of large width and the remaining loaders 42 may be loaded with the imaging apparatuses 2A of small width, or as shown in FIG. 8C, a certain one loader 42 may be loaded with the imaging apparatus 2A of small width and the remaining loaders 42 may be loaded with the imaging apparatuses 2B of large width.

That is, the radiographic imaging system 100 according to the present embodiment can be configured such that at least one of the plurality of imaging apparatuses 2 has a width in the direction orthogonal to the direction of arrangement and the thickness direction of the own apparatus, which is different from the others.

Of course, it will be all right if all the imaging apparatuses 2 to be loaded are imaging apparatuses 2B of large width or imaging apparatuses 2A of small width.

As described above, the width of the loader 42 is shorter than the imaging apparatus 2B of large width. Therefore, when the imaging apparatus 2A of small width is inserted until one end thereof in the width direction comes into contact with the back of the loader 42, the imaging apparatus 2B can be fitted in the loader 42 up to the other end, whereas even when the imaging apparatus 2B of large width is inserted until one end thereof comes into contact with the back of the loader 42, part of the imaging apparatus 2B sticks out to the side of the holder 4.

[Image Processing Apparatus]

Figure 9:
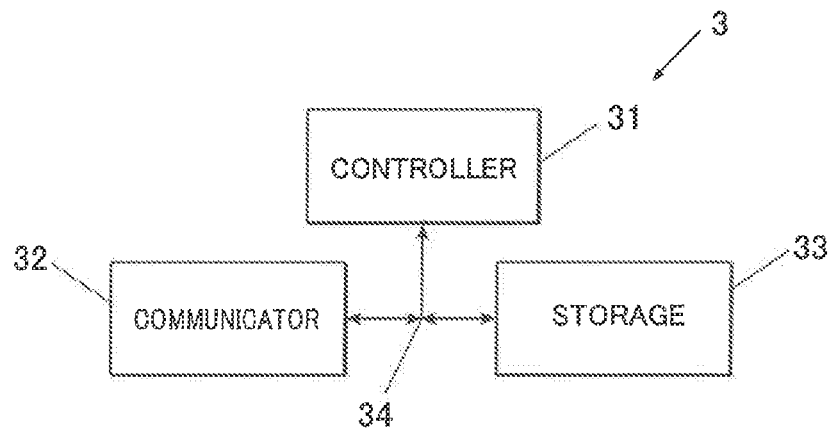
FIG. 9 is a block diagram illustrating an electrical configuration of the image processing apparatus provided for the radiographic imaging system in FIG. 1.

Next, details of the image processing apparatus 3 constituting the radiographic imaging system 100 will be described. FIG. 9 is a block diagram illustrating a configuration of the image processing apparatus 3.

As shown in FIG. 9, the image processing apparatus 3 is constructed of a controller 31, a communicator 32 and a storage 33, and the respective parts 31 to 33 are connected via a bus 34.

Note that the image processing apparatus 3 may also be provided with a display that can display images or a function that allows the image processing apparatus 3 to be connected to an external display apparatus to display images.

Furthermore, the image processing apparatus 3 may be provided with an operator that can be manipulated by a user. More specifically, examples of the operator include a keyboard provided with various keys, a pointing device such as a mouse and a touch panel laminated on the display.

The controller 31 is configured to integrally control operation of each part of the image processing apparatus 3 through a CPU and a RAM or the like. More specifically, the controller 31 reads various programs stored in the storage 33, develops the programs on the RAM, executes various processes according to the programs and controls display contents of the display.

The communicator 32 is constructed of a network interface or the like and transmits/receives data to/from an external apparatus connected via a communication network such as a LAN, a WAN and the Internet. Note that the communicator 32 may perform radio communication using a mobile phone channel or the like to transmit/receive data to/from an external apparatus connected via a communication network.

The storage 33 is constructed of an HDD (hard disk drive) and a semiconductor memory or the like and stores programs to execute various types of processing including image combining processing which will be described later, parameters and files necessary to execute these programs.

Figure 10:
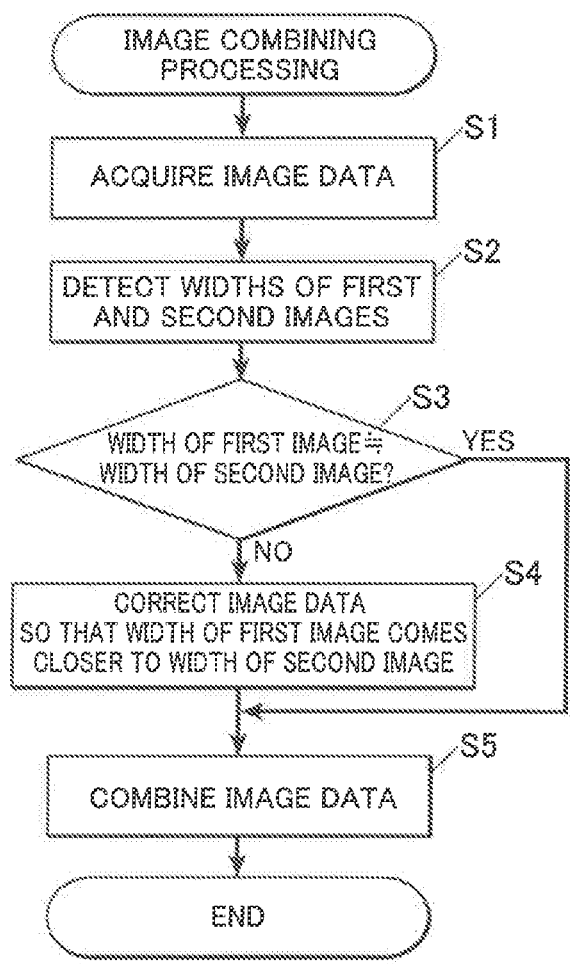
FIG. 10 is a flowchart illustrating image combining processing executed by the image processing apparatus in FIG. 9.

The controller 31 of the image processing apparatus 3 configured as described above has a function of performing image combining processing shown, for example, in FIG. 10 according to the program stored in the storage 33. This image combining processing is executed triggered by reception of an operation signal from the operator or reception of various signals or image data from the imaging apparatus 2.

In the image combining processing, a plurality of imaging apparatuses 2 arranged so as to form a line along an imaging target region of a subject and generating image data of radiographic images by receiving radiation acquire first image data and second image data which is different from the first image data from among the plurality of pieces of image data generated by receiving radiation via the imaging target region first (step S1).

In the present embodiment, image data is acquired from the plurality of imaging apparatuses 2 loaded into the holder 4 via the communicator 32.

That is, the controller 31 and the communicator 32 constitute an image acquirer in the present invention.

Next, in a first image $I_1$ based on the acquired first image data and a second image $I_2$ based on second image data, the width in the detection orthogonal to the direction in which these images are arranged in a line is detected (step S2).

That is, the controller 31 constitutes a width detector in the present invention.

Next, the detected width of the first image $I_1$ is compared with the width of the second image $I_2$ to determine whether or not the widths of both images match (step S3).

In the processing, both widths need not completely match and if the difference between both images falls within several millimeters, both widths are preferably considered to be the same.

In step S3, when both widths are determined to match (step S3; Yes), the flow moves to step S5, which will be described later.

On the other hand, in step S3, when both widths are determined to be different (step S3; No), at least one of the first image data and the second image data is corrected so that both widths come closer to each other (step S4).

In the present embodiment, using the width of the first image $I_1$ as a reference, the width of the second image $I_2$ is brought closer to the width of the first image $I_1$ from the standpoint of simplifying processing.

In this step S4, when the comparison result shows that when the detected width of the second image $I_2$ is larger than the width of the first image $I_1$, the first image data is corrected so that when the first image $I_1$ and the second image $I_2$ are arranged side by side, a width of a region $I_{2a}$ in the second image $I_2$ which sticks out from the first image $I_1$ in the width direction is reduced.

In that case, as shown in FIG. 11A and FIG. 11B, it is preferable to make a correction so that the region $I_{2a}$ sticking out in the width direction is cut, that is, make a correction so that the width of the region $I_{2a}$ is reduced to 0 and both ends of the first and second images $I_1$ and $I_2$ in the width direction are aligned with each other.

Examples of such a correction include a case where as shown in FIG. 11A, the regions $I_{2a}$ sticking out to both sides in the width direction of the second image $I_2$ are cut and a case where as shown in FIG. 11B, one ends of both images $I_1$ and $I_2$ are aligned in advance and only the region $I_{2a}$ sticking out to the other end side is cut.

Note that in this step S4, when the comparison result shows that the detected width of the second image $I_2$ is smaller than the width of the first image $I_1$, the first image data may be corrected so that when the first image $I_1$ and the second image $I_2$ are arranged side by side, at least part of a region $R_2$ where no image exists, generated between an end of the second image $I_2$ in the width direction and an extension line $L_1$ extending from an end of the first image $I_1$ in the width direction in a direction in which these images are arranged side by side, may be interpolated as a portion $I_{2b}$ of the second image $I_2$.

Figure 12A:
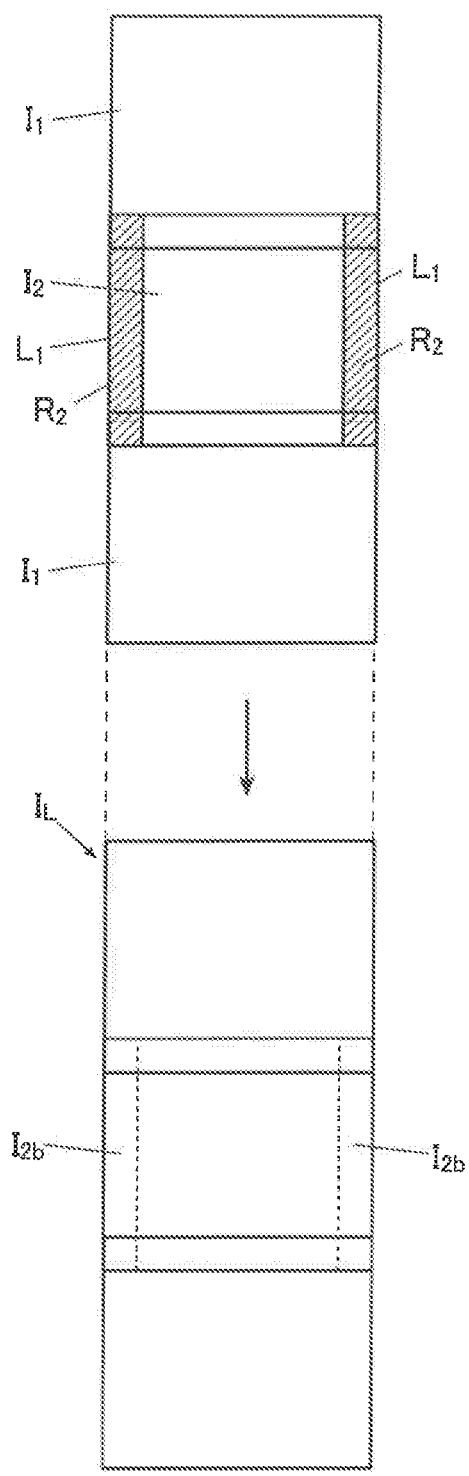
FIG. 12A is a conceptual diagram illustrating an image data correction method.
Figure 12B:
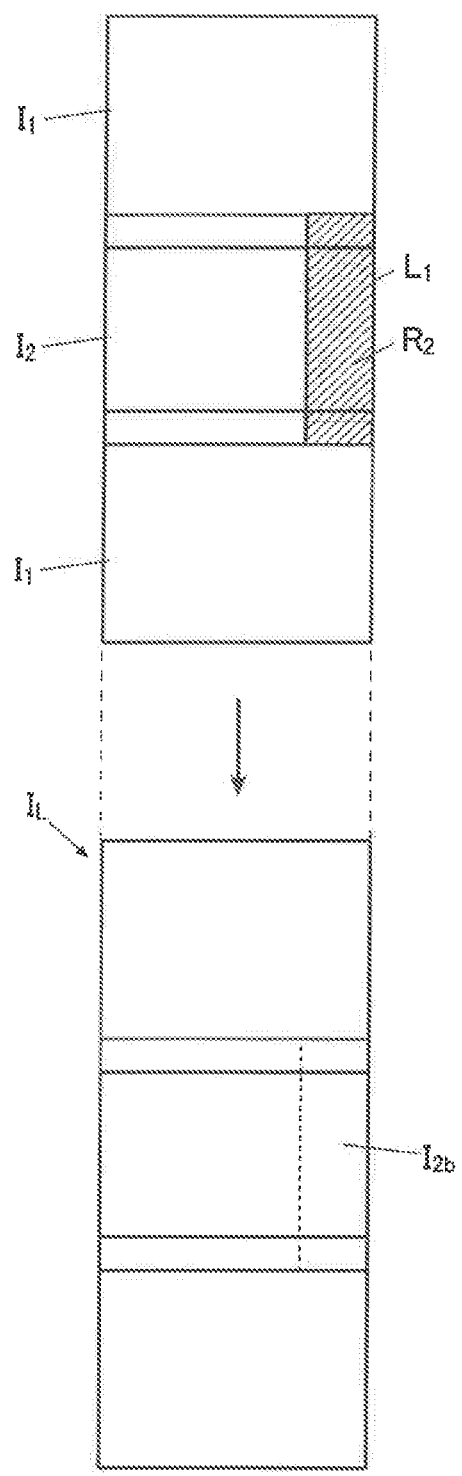
FIG. 12B is a conceptual diagram illustrating an image data correction method.

In that case, as shown in FIG. 12A and FIG. 12B, it is preferable to make a correction so that the whole region $R_2$ where this image does not exist is interpolated as a portion $I_{2b}$ of the second image $I_2$, that is, to make a correction so that both ends of the first and second images $I_1$ and $I_2$ in the width direction are aligned with each other.

Examples of the correction include a case where as shown in FIG. 12A, both regions $R_2$ where no image exists, generated on both sides of the second image $I_2$ are interpolated and a case where as shown in FIG. 12B, one ends of both images $I_1$ and $I_2$ are aligned with each other in advance and only the region $R_2$ where no image exists, generated on the other end sides of the second image $I_2$ is interpolated.

The controller 31 that performs such processing constitutes a corrector in the present invention.

After step S4, as shown in FIG. 10, a plurality of pieces of image data including the corrected image data are combined to thereby generate one lengthy piece of image data (step S5).

A method of combining a plurality of pieces of image data is not particularly limited, but when both ends of the first image $I_1$ and the second image $I_2$ in the width direction are aligned in step S3, it is possible to use the technique described in aforementioned Japanese Patent Laid-Open No. 2013-154146.

More specifically, a profile (tendency of a change of a signal value) of the image data seen in the width direction in the overlapping region at the top end portion of the lower image among the pieces of image data is calculated. Then, a profile of the image data in the overlapping region at the bottom end portion of the upper image which overlaps with the overlapping region is likewise calculated. In each overlapping region, an end portion (edge) in the lateral direction of the patients body in the image is detected. In the respective overlapping regions where images overlap each other, both images are coupled so that the positions of the detected edges match in the width direction and the respective images in the direction in which the images are arranged side by side overlap with each other by the amount of overlapping. By repeating this processing the number of times corresponding to the number of times imaging is performed, one piece of lengthy image data is obtained.

The controller 31 that performs such processing constitutes an image combiner in the present invention.

In the present invention, when the widths of both images $I_1$ and $I_2$ are not aligned with each other, the image data is corrected as described above. Since the corrected part, the interpolated part in particular is interpolated with black, white or gray images which are different from the captured images $I_1$ and $I_2$ and are images artificially generated, using these regions to calculate the coupling position, the images may be coupled at a wrong coupling position.

However, by detecting the edges and using the edges for positioning (without using the corrected part for positioning), it is possible to obtain lengthy images $I_L$ coupled at a correct position.

Note that a case has been described so far where images are combined in combination of images of two widths: large and small, but the present invention is also applicable to combinations of images of three or more widths: large, medium and small.

More specifically, as shown, for example, in FIG. 13A, an image of medium size may be designated as a first image $I_1$ to serve as a reference, a protruding region $I_{2a}$ of a second image $I_2$ of large width may be cut, and a region $R_3$ where no image exists on the side of a third image $I_3$ of smaller width than the first image can be complemented. Alternatively, as shown in FIG. 13B, an image of smallest width may be designated as a first image $I_1$ to serve as a reference, protruding regions $I_{2a}$ and $I_{3a}$ of second and third images $I_2$ and $I_3$ of larger width may be all cut, or as shown in FIG. 13C, an image of the largest width may be designated as a first image $I_1$ to serve as a reference and regions $R_2$ and $R_3$ where no image exists on the side of second and third images $I_2$ and $I_3$ of smaller width can be all interpolated.

[Lengthy Imaging]

Next, the method for radiographic lengthy imaging using the imaging apparatus 2 will be described.

First, the holder 4 is prepared. In the case of standing imaging, the holder 4 is attached to a support 5 so as to stand thereon. In the case of lying imaging, the holder 4 is placed on a bed or floor.

Next, a plurality of imaging apparatuses 2 are loaded into the respective loaders 42 of the holder 4. In that case, by causing each imaging apparatus 2 to come into contact with the back of each loader 42, the plurality of imaging apparatuses 2 are arranged side by side such that one ends in the width direction are aligned with each other.

Next, the body 41 of the holder 4 or a plug 43a of the cable 43 extending from the support 5 is inserted into the connector 25a of each imaging apparatus 2 and each imaging apparatus 2 is connected to the image processing apparatus 3.

Next, a subject is placed between the radiation exposure apparatus 1 and the holder 4 and the subject is positioned. In this way, a plurality of imaging apparatuses are arranged in a line along an imaging target region of the subject and preparations for imaging are completed.

When preparations are completed, the exposure switch 12 is pressed. Radiation is then radiated from the radiation source 13 onto the subject and the plurality of imaging apparatuses 2 (holders 4) behind the subject, each imaging apparatus 2 generates image data of radiographic images and the image data is transferred to the image processing apparatus 3.

The image processing apparatus 3 performs the aforementioned image combining processing to generate one lengthy piece of image data. When the widths of the imaging apparatuses 2 used are not aligned with one another, processing is performed to bring the widths of the respective images close to one another in this image combining processing (see step S4 in FIG. 10).

After that, if necessary, a lengthy image $I_L$ based on the generated lengthy image data is displayed on a display (not shown) provided for the image processing apparatus 3 or a display apparatus (not shown) connected to the image processing apparatus 3.

As described so far, the image processing apparatus 3 according to the present embodiment is provided with an image acquirer that acquires first image data and image data different from the first image data from among a plurality of pieces of image data generated by a plurality of imaging apparatuses 2 by receiving radiation via an imaging target region of a subject, the plurality of imaging apparatuses 2 being arranged so as to form a line along the imaging target region of the subject to generate image data of radiographic images by receiving radiation, a width detector that detects widths of a first image $I_1$ based on the first image data acquired by the image acquirer and a second image $I_2$ based on the second image data in a direction orthogonal to the direction in which the first and second images are arranged side by side, a corrector that corrects, when the width of the first image $I_1$ detected by the width detector is different from the width of the second image $I_2$, at least one piece of the image data of the first image data and the second image data so that both widths are brought closer to each other and an image combiner that combines a plurality of pieces of image data including the image data corrected by the corrector to thereby generate one lengthy piece of image data.

When widths of images based on the respective pieces of image data to be combined are not aligned with one another, it is difficult to combine the images. However, when the plurality of pieces of image data are combined to generate one lengthy piece of image data, if the image processing apparatus 3 according to the present embodiment is used to correct the image data so that widths of the respective images are brought closer to each other, it is possible to easily combine the respective pieces of image data even when the respective pieces of image data have different sizes.

Furthermore, when widths of the respective images are different, there are such problems as: conventional image combining techniques cannot be used, and irregularities are generated on the long side of the lengthy image $I_L$ based on the combined lengthy image data which is visually awkward. However, by correcting the image data so that the widths of the respective images are aligned with one another using the image processing apparatus 3 according to the present embodiment, it is possible to use the conventional image combining technique, combine images more easily and since the lengthy image $I_L$ based on the generated lengthy image data becomes rectangular, the appearance improves.

Example 1

Next, problems which are estimated to newly arise when the present invention is implemented as described in the above embodiments and specific examples where such problems can be solved will be enumerated hereunder.

Example 1

When performing lengthy imaging using the above radiographic imaging system 100, a grid 6 may be provided on the radiation incident plane 41a of the holder 4 (closer to the radiation exposure apparatus 1 side than the imaging apparatus 2). The grid 6 includes a plurality of slits arranged side by side so as to extend parallel to one another when seen from a direction orthogonal to the plane in contact with the holder 4 and is configured to restrict scattered radiation included in the radiated radiation from entering the imaging apparatus 2.

In that case, if a slit positioned at the center among the plurality of slits in the grid 6 is not aligned with the center in the width direction of the radiation incident plane 21d (effective imaging region R1) of the imaging apparatus 2, the system is affected by scattered radiation and density unevenness occurs in the image generated, and so it is necessary to align the center of the grid 6 with the center of the radiation incident plane 21d.

However, when the imaging apparatuses 2A and 2B of different widths are loaded into the same holder 4 and used, it is difficult to achieve alignment between the respective centers.

In view of such a problem, the grid 6 may be configured to have the same width as the width of the imaging apparatus 2A of the smallest width as shown in FIG. 14 to be disposed on the radiation incident plane 41a of the holder 4. That is, a plane passing through a center C in the width direction of the loader 42 and orthogonal to the width direction may be disposed on the radiation incident plane 41a of the holder 4 such that the plane passes through a slit Sc positioned at the center among the plurality of slits, and when the imaging apparatus 2A of smaller width is loaded, the center C of the grid 6 may be aligned with the center of the imaging apparatus 2A.

In that case, the portion protruding sideward from the imaging apparatus 2B of larger width is prevented from being used for imaging.

In this way, it is possible to align the slit at the center of the grid 6 with the center in the width direction of the imaging apparatus 2 without being conscious of the widths of the imaging apparatuses 2A and 2B.

Furthermore, since the size of the grid 6 can be reduced, the manufacturing cost of the grid can be reduced and carrying the grid 6 can be made easier because such a grid 6 weighs less.

Example 2

In imaging using the holder 4 according to the above-described embodiment, part of the imaging apparatus 2B of large width sticks out as described above. Thus, when the holder 4 is loaded with the imaging apparatus 2B to image a lying subject, if the holder 4 is placed on the floor, the user or subject may step on the protruding portion of the imaging apparatus 2B, the user or subject may fall down or the imaging apparatus 2B may be damaged.

On the other hand, when the holder 4 is placed at a position higher than the floor such as a bed, the user or subject may bump his/her leg against the protruding portion of the imaging apparatus 2B.

Figure 15A:
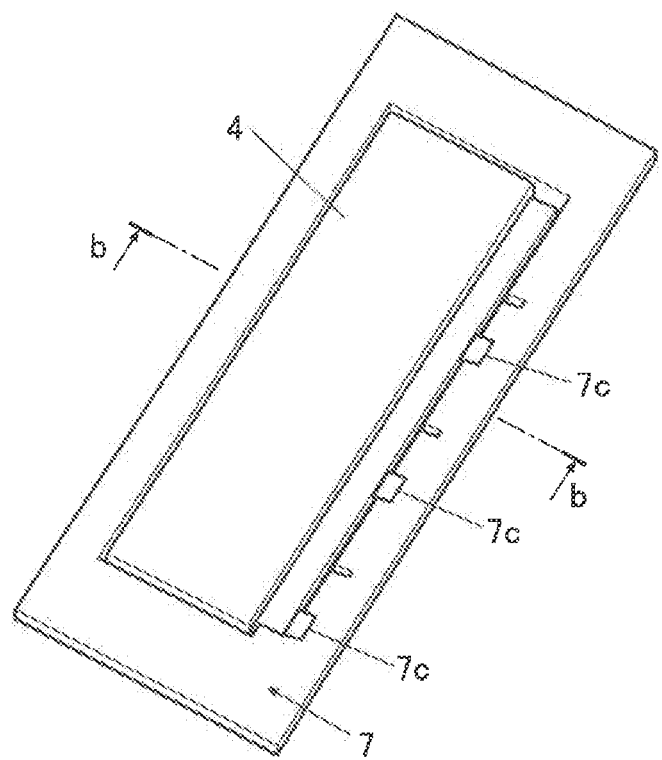
FIG. 15A is a perspective view of a radiographic imaging apparatus, a holder and a protective member provided for a radiographic imaging system according to example 2 of the embodiment.
Figure 15B:
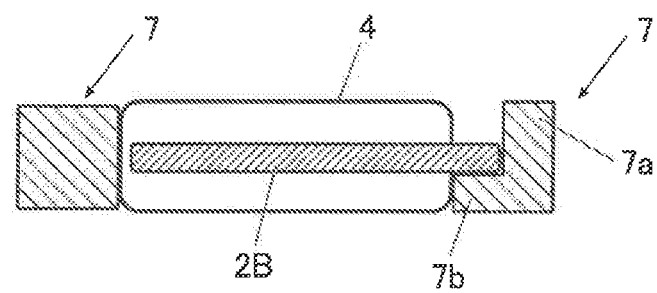
FIG. 15B is a cross-sectional view of the radiographic imaging apparatus, the holder and the protective member provided for the radiographic imaging system according to example 2 of the embodiment.

In view of such a problem, a protective member 7 for protecting the protruding portion of the imaging apparatus 2B may be attached to the holder 4 as shown, for example, in FIG. 15A or FIG. 15B. Note that although FIG. 15A illustrates the protective member 7 that covers the whole circumference of the holder 4, the protective member 7 may include at least a side face protector 7a that covers the IF surface 21e of the imaging apparatus 2B and a rear face protector 7b that covers the rear face of the protruding portion as shown in FIG. 15B.

The side face protector 7a may be preferably provided with a recessed portion to prevent the side face protector 7a from shielding the connector 25a.

In lying imaging, it is thereby possible to prevent the user or subject from stepping on the protruding portion of the imaging apparatus 2B or bumping his/her leg or the like against the protruding portion.

When the holder 4 is loaded with the imaging apparatus 2A of small width together with the imaging apparatus 2B of large width, a space is produced between the side face protector of the protective member 7 and the imaging apparatus 2A of small width, the space corresponding to an amount of the portion of the imaging apparatus 2A that does not protrude sideward from the holder 4. Therefore, an attachment may be fitted into the space for such a mode of use.

Example 3

In imaging using the holder 4 according to the above embodiment, the position of the connector 25a of the imaging apparatus 2 relative to the holder 4 varies depending on the size of the imaging apparatus 2. More specifically, when the holder 4 is loaded with the imaging apparatus 2A of small width, the connector 25a of the imaging apparatus 2A is positioned in the vicinity of the loading port 42a. On the other hand, when the holder 4 is loaded with the imaging apparatus 2B of large width, the connector 25a of the imaging apparatus 2B is positioned away from the loading port 42a.

Thus, while the plug 43a of the cable 43 provided for the holder 4 can be inserted into the connector 25a of the imaging apparatus 2A of small width, the plug 43a of the cable 43 may not be able to reach the connector 25a of the imaging apparatus 2B of large width.

Figure 16A:
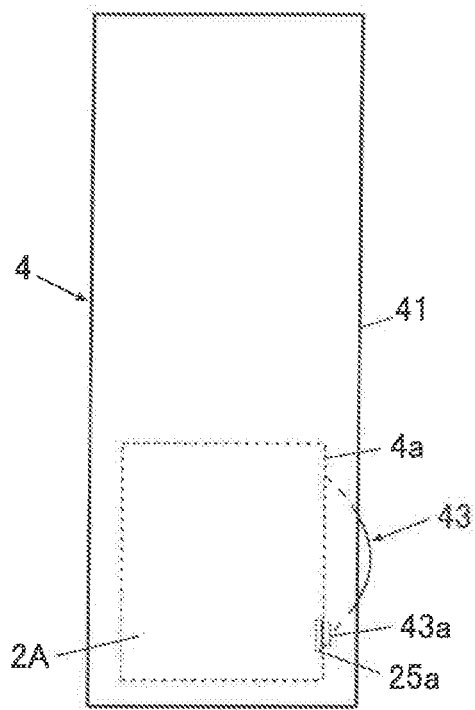
FIG. 16A is a front view of a radiographic imaging apparatus and a holder provided for a radiographic imaging system according to example 3 of the embodiment.
Figure 16B:
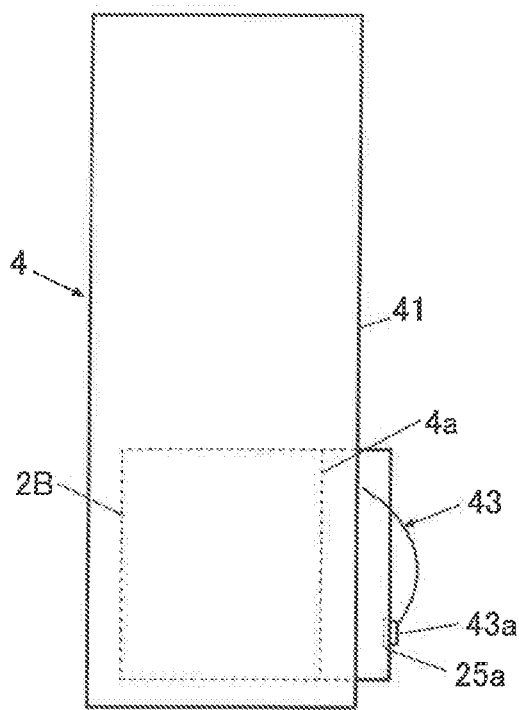
FIG. 16B is a front view of another radiographic imaging apparatus and another holder provided for the radiographic imaging system according to example 3 of the embodiment.

In view of the above problem, the length of the cable 43 from the body 41 to the plug 43a may be preferably set to be long enough to reach the connector 25a of the imaging apparatus 2B of largest width that can be loaded as shown, for example, in FIG. 16A and FIG. 16B.

In this way, irrespective of the widths of the imaging apparatuses 2A and 2B loaded into the holder 4, the plug 43a of the cable 43 can be inserted into the connector 25a.

Note that the holder 4 may be provided with a plurality of cables 43 of different lengths according to the widths of the imaging apparatuses 2A and 2B.

Example 4

Which imaging apparatus 2 is loaded in which stage of the holder 4 can be recognized by connecting the corresponding cable 43 provided in each stage to the imaging apparatus 2 or to a wireless ID-Key, but if the cable 43 provided in a certain stage can be connected to (or can reach) the imaging apparatuses 2 in different stages, the image processing apparatus 3 may erroneously recognize the imaging apparatus 2, which may cause image combining to fail.

Figure 17A:
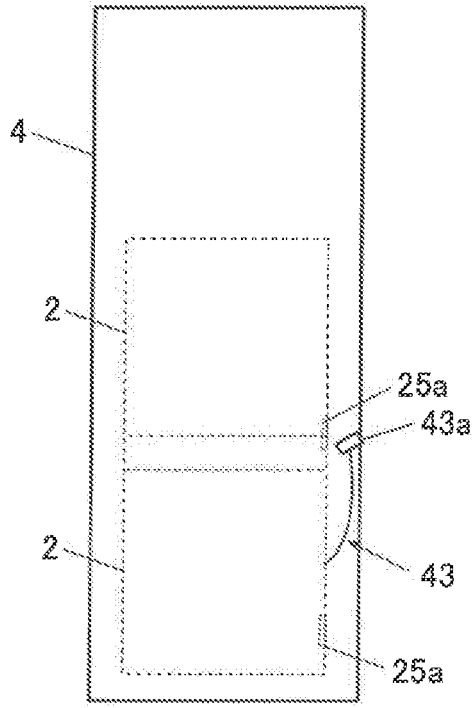
FIG. 17A is a front view of a radiographic imaging apparatus and a holder provided for a radiographic imaging system according to example 4 of the embodiment.

In view of such a problem, as shown, for example, in FIG. 17A, the cable 43 may be configured to have a length which does not allow the plug 43a of the cable 43 provided in each stage to reach the imaging apparatus 2 loaded in a stage different from the stage in which the cable 43 itself is provided.

Figure 17B:
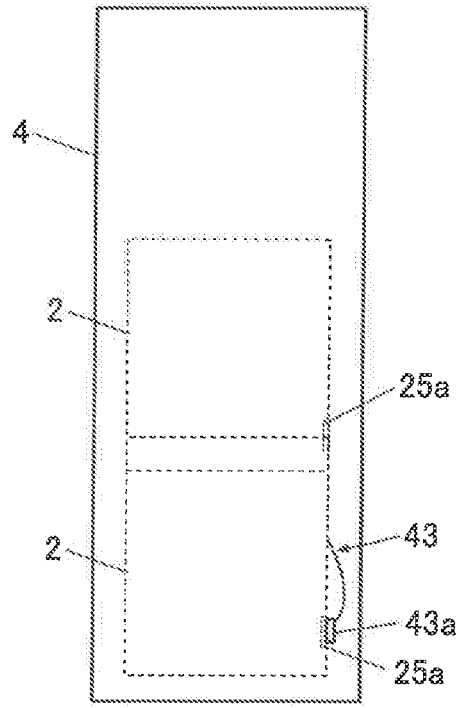
FIG. 17B is a front view of the radiographic imaging apparatus and the holder provided for the radiographic imaging system according to example 4 of the embodiment.

With such a configuration, each cable 43 can only be connected to (can only reach) the imaging apparatus 2 loaded in the stage in which the cable 43 itself is provided as shown in FIG. 17A, and so each cable 43 is always connected to the correct imaging apparatus 2 as shown in FIG. 17B, making it possible to prevent the image processing apparatus 3 from erroneously recognizing the imaging apparatus 2.

Example 5

When lengthy imaging is performed with some imaging apparatuses 2 insufficiently loaded, the position of the subject in the width direction in images generated by each imaging apparatus 2 may differ. If this happens, image combining may not be successfully performed and re-imaging may be needed, which may cause the subject to be exposed uselessly.

In order to avoid such problems, a countermeasure such as providing in the vicinity of each loading port 42a, a lock mechanism for pressing the imaging apparatus 2 against the back of the body 41 may be considered.

However, the holder 4 according to the above embodiment can be loaded with the imaging apparatuses 2A and 2B of different widths as described above, and the position of the IF surface 21e during loading differs between the imaging apparatus 2A of small width and the imaging apparatus 2B of large width. For this reason, if a lock mechanism is provided in accordance with the large (small) width of the imaging apparatus 2B (2A), it is not possible to press the imaging apparatus 2A (2B) of small (large) width.

Figure 18A:
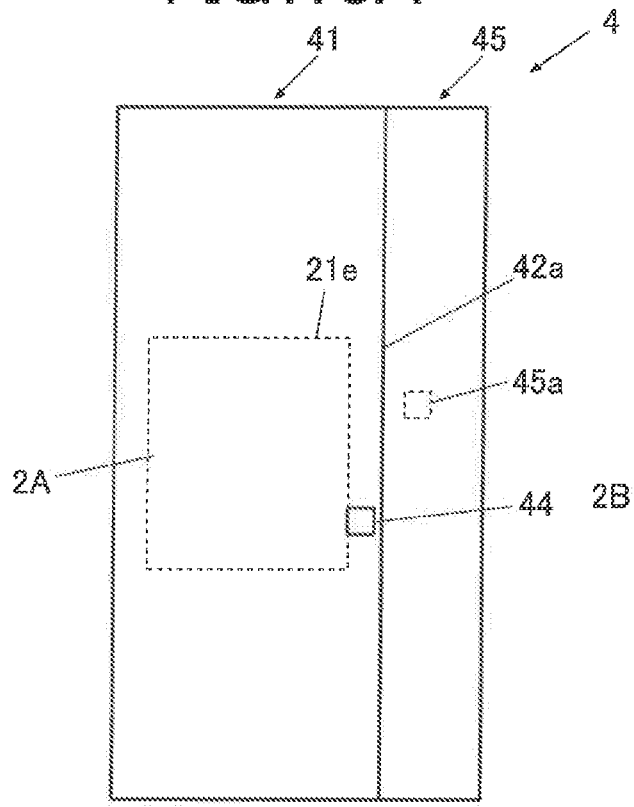
FIG. 18A is a front view of a radiographic imaging apparatus and a holder provided for a radiographic imaging system according to example 5 of the embodiment.
Figure 18B:
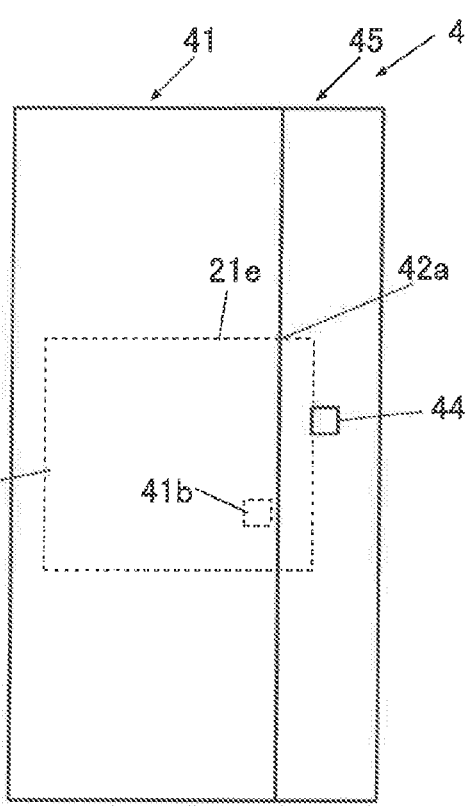
FIG. 18B is a front view of the radiographic imaging apparatus and the holder provided for the radiographic imaging system according to example 5 of the embodiment.

In view of such a problem, as shown, for example, in FIG. 18A or FIG. 18B, a lock member 44 may be detachably attached at a location corresponding to the IF surface 21e in the vicinity of each loading port 42a of the holder 4 when loaded with the respective imaging apparatuses 2A and 2B of different widths.

More specifically, an engagement part 41b or 45a is formed in the vicinity of the IF surface 21e when the body 41 or the cover 45 provided at the side of the body 41 is loaded with each imaging apparatus 2A or 2B of different widths and the loader 42 is loaded with the imaging apparatus 2, and then the lock member 44 is made to engage with the engagement part 41b or 45a located in the vicinity of the IF surface 21e of the loaded imaging apparatus 2 so as to be in contact with the IF surface 21e.

With such a configuration, the imaging apparatus 2 is pushed into the back of the holder 4 irrespective of the width thereof, making it possible to prevent positional displacement of the imaging apparatus 2.

Note that an elastic member or the like may be used so as to allow the imaging apparatus 2 to be loaded to the back irrespective of the width thereof.

A sensor or the like may be used to detect whether or not the imaging apparatus 2 has been loaded to the back, and when the imaging apparatus 2 has not been loaded, the sensor may inform the fact.

Example 6

Figure 19A:
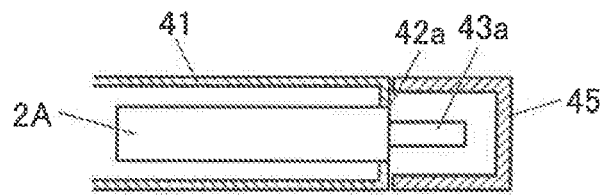
FIG. 19A is a cross-sectional view of the radiographic imaging apparatus and the holder provided for the radiographic imaging system according to the embodiment.

As shown, for example, in FIG. 19A, when the loading port 42a of the imaging apparatus 2 in the holder 4 provided with a cover 45 for opening/closing the loading port 42a is used, if the imaging apparatus 2B of large width is loaded, the imaging apparatus 2B may stick out of the loading port 42a of the holder 4, interfering with the cover 45 and preventing the cover 45 from being closed.

Figure 19B:
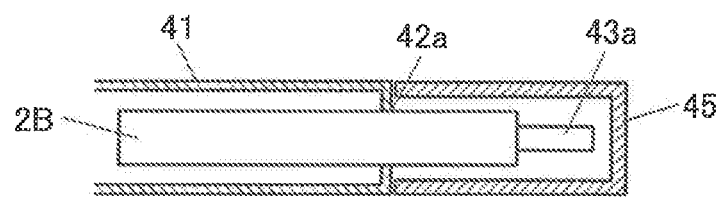
FIG. 19B is a cross-sectional view of a radiographic imaging apparatus and a holder provided for a radiographic imaging system according to example 6 of the embodiment.

In view of such a problem, as shown, for example, in FIG. 19B, the cover 45 of the holder 4 may be configured to have a shape extended sideward to such an extent as to cover the protruding portion of the imaging apparatus 2B of large width.

Note that the cover 45 may be preferably large enough to accommodate the plug 43a of the cable 43 as well.

With such a configuration, when the holder 4 is loaded with the imaging apparatus 2B of large width, even if part of the imaging apparatus 2B sticks out of the loading port 42a, the protruding portion can be covered with the cover 45, and it is thereby possible to close the cover 45.

Example 7

The cover 45 of the holder 4 may interfere with an obstacle O (imaging apparatus 2, cable 43, external auxiliary tool or the like), which may make it difficult to open/close the cover 45.

Figure 20:
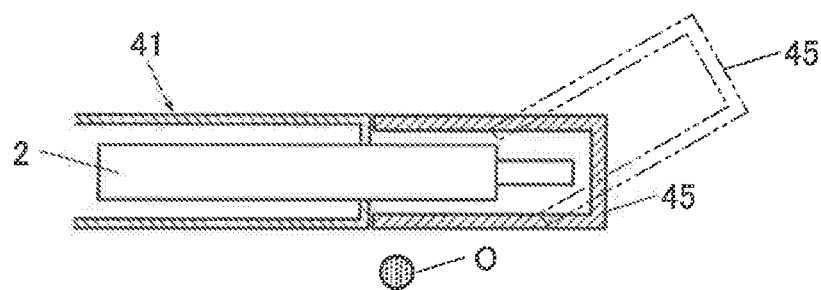
FIG. 20 is a cross-sectional view of a radiographic imaging apparatus and a holder provided for a radiographic imaging system according to example 7 of the embodiment.

In view of such a problem, the cover 45 may be configured to be attachable/detachable to/from the body 41 as shown by a broken line in FIG. 20, for example, so that the cover 45 may be opened/closed after avoiding the obstacle O.

Note that a configuration that causes the obstacle O to retract may also be adopted.

With such a configuration, the cover 45 will not interfere with the imaging apparatus 2, the cable 43 or the external obstacle O, making it possible to easily open/close the cover 45.

Example 8

When the holder 4 of the above embodiment is provided with the cover 45 that can cover the protruding portion of the imaging apparatus 2B of large width as shown in example 6, the center of gravity of the holder 4 is moved by an amount corresponding to the weight of the cover 45 in the direction in which the imaging apparatus 2B sticks out. When such a holder 4 is attached to the support 5 provided with a lifting mechanism and used, an excessive load is applied to the lifting mechanism of the support 5.

Furthermore, the center of the body 41 in the width direction is deviated from the center of the whole holder 4 including the cover 45 in the width direction, and so the subject cannot know whether his/her body axis should be aligned with the center of the body 41 in the width direction or the center of the holder 4 in the width direction.

Moreover, with the cover 45 attached, the appearance of the holder 4 may become laterally asymmetric and people may feel that holder 4 is visually awkward.

Figure 21A:
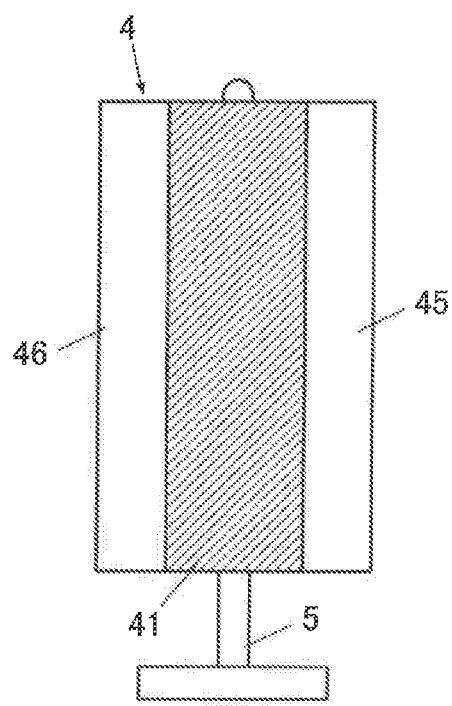
FIG. 21A is a front view of a holder provided for a radiographic imaging system according to example 8 of the embodiment.
Figure 21B:
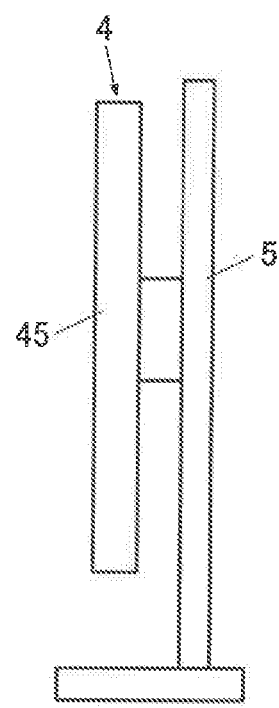
FIG. 21B is a side view of the holder provided for the radiographic imaging system according to example 8 of the embodiment.

In view of such a problem, a decorative member 46 having a shape laterally symmetric to the cover 45 may be attached to the side face opposite to the side face of the body 41 to which the cover 45 is attached as shown, for example, in FIG. 21A.

With such a configuration, the center of gravity of the holder 4 approaches the center of the body 41 in the width direction, and it is thereby possible to reduce the load applied to the lifting mechanism when the holder 4 is attached to the support 5 provided with the lifting mechanism.

Furthermore, the center of the body 41 in the width direction matches the center of the whole holder 4 in the width direction, and so the subject can perform alignment more easily.

Moreover, the holder 4 becomes laterally symmetric, which improves the appearance of the holder 4.

Example 9

The cable 43 may interfere with the obstacle O (e.g., lock member 44 and hand grip or the like) inside the cover 45 preventing the cover 45 from being opened/closed.

Figure 22:
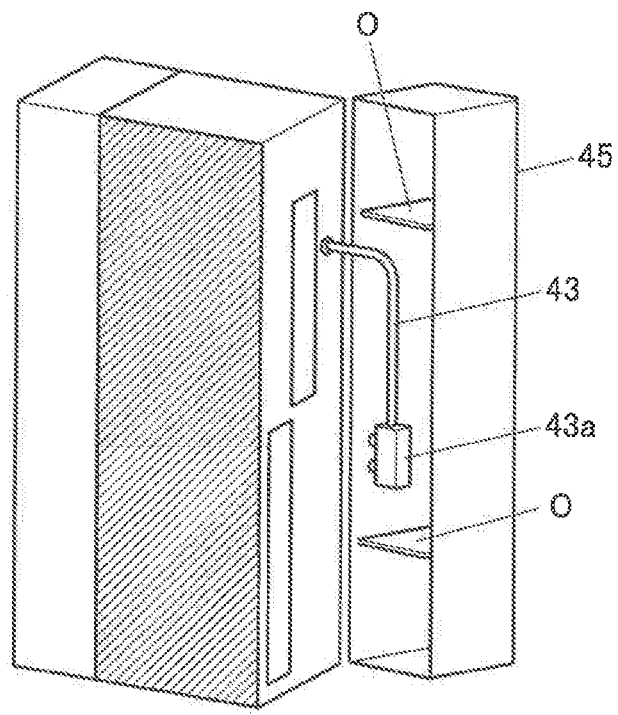
FIG. 22 is a perspective view illustrating a holder provided for a radiographic imaging system according to example 9 of the embodiment.

In view of such a problem, as shown, for example, in FIG. 22, the obstacle O (e.g., aforementioned lock member 44) may not be disposed within a movable range of the cable 43 of the imaging apparatus 2 recognition block when the cable 43 or wireless communication is used.

With such a configuration, the cover 45 can be opened/closed without the cable 43 interfering with the obstacle O.

Example 10

Figure 23:
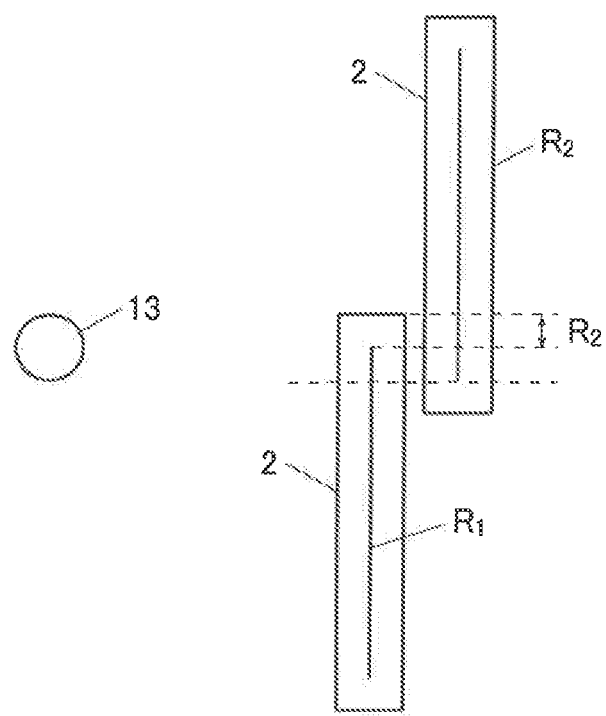
FIG. 23 is a side view for describing a correction region.

In lengthy imaging using the holder 4 according to the above embodiment, the effective imaging region R1 of one imaging apparatus 2 partially overlaps that of the other imaging apparatus 2 when seen from the radiation source 13 (seen from a direction orthogonal to the radiation incident plane 41a) as shown in FIG. 23, and therefore the anterior imaging apparatus 2 is imaged inside part of the overlapping region (hereinafter referred to as "correction region $R_2$") of an image imaged by the imaging apparatus 2 located at a relatively posterior (here above) position. For the overlapping region other than the correction region $R_2$, the image of the anterior imaging apparatus 2 can be used, and so there is no problem, whereas it is not possible to apply sufficient image processing to the correction region $R_2$, and so the image of the anterior imaging apparatus 2 may remain in the image of the posterior apparatus, leaving a possibility that an image diagnostician may mistake it for a lesion.

Figure 24:
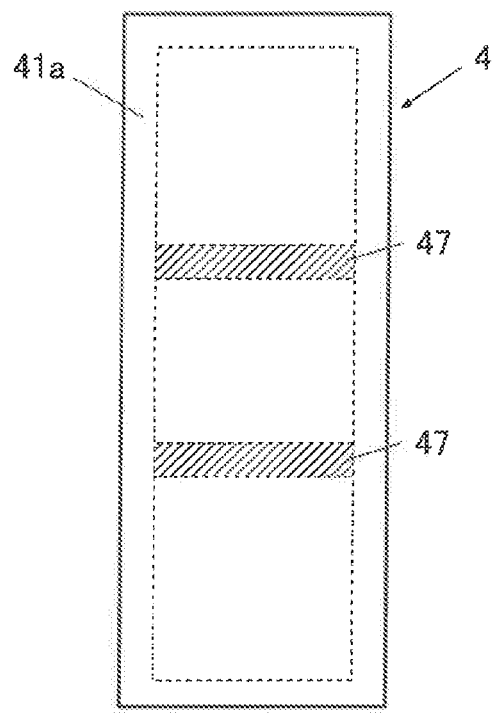
FIG. 24 is a front view of a holder provided for a radiographic imaging system according to example 10 of the embodiment.

In view of such a problem, an overlapping region indicating marker 47 may be provided in a region that overlaps the overlapping region of the radiation incident plane 41a of the holder 4 when seen from a direction orthogonal to the radiation incident plane 41a as shown, for example, in FIG. 24 and may be displayed on the lengthy image $I_L$ generated.

With such a configuration, by looking at the marker 47 attached to the radiation incident plane 41a of the holder 4, the user can perform imaging while recognizing that the part indicated by the marker becomes the overlapping region to which image processing is applied.

With the marker 47 displayed in the lengthy image $I_L$ generated, the user or image diagnostician can recognize in advance that the anterior imaging apparatus 2 is imaged inside the overlapping region, and can thereby prevent the image of the anterior imaging apparatus 2 which has not been successfully removed through image processing from being mistaken for a lesion.

Example 11

In order to specify the overlapping region using the marker 47, the marker 47 needs to be imaged inside the image. In order for the marker 47 to be imaged inside the image, the marker 47 needs to be located within an irradiation field range.

In view of such a problem, the position of the marker 47 may be configured to be adjustable.

More specifically, locking faces for a surface fastener may be provided at side end portions of the radiation incident plane of the body 41 and locked faces of the surface fastener may be provided at both ends of the marker 47 so that the marker 47 may be made attachable/detachable to/from the body 41, may be made movable by the user's hand or may be automatically movable by an actuator operating based on radiation light for determining the position of irradiation before imaging or information or the like sent from a collimator.

With such a configuration, the marker 47 can be located within the irradiation field and the marker 47 can be imaged inside the image.

Example 12

When imaging is performed based on the effective imaging region R1 of the imaging apparatus 2B of large width (maximizing the area of the imaging surface), if the imaging apparatus 2 of small width is also used together, positioning of the grid 6 becomes difficult.

Figure 25:
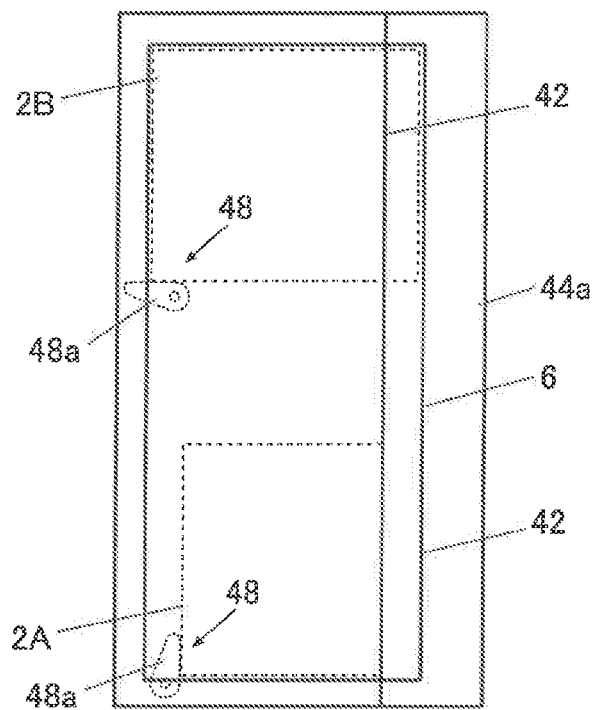
FIG. 25 is a front view of a radiographic imaging apparatus and a holder provided for a radiographic imaging system according to example 12 of the embodiment.

In view of such a problem, for example, a grid 6 having the same width as that of the imaging apparatus 2B of large width may be used and, when the imaging apparatus 2A of small width is loaded at the back of each loader 42 of the holder 4 as shown, for example, in FIG. 25, a stopper mechanism 48 may also be provided for restricting the imaging apparatus 2A of small width from being further inserted at a point at which the center of the imaging apparatus 2A in the width direction coincides with the center in the width direction of the imaging apparatus 2B of large width to be loaded into the loader 42.

The stopper mechanism 48 is configured as shown, for example, in FIG. 25 such that a stopper 48a rotates to an upright position (moves along the side face of the imaging apparatus 2A) when the imaging apparatus 2 of small width is loaded or the stopper 48a falls down (moves along the undersurface of the imaging apparatus 2B or along the undersurface of the loader 42) when the imaging apparatus 2 is not loaded or when the imaging apparatus 2B of large width is loaded.

Examples of the method of recognizing the width of the imaging apparatus 2 include marking, weight measurement or width measurement.

With such a configuration, if the width of the grid 6 is aligned with the center of one of the imaging apparatuses 2, the width of the grid 6 is also aligned with the center in the width direction of the other imaging apparatus 2, and so it is possible to make the grid 6 aligned with the center in the width direction of the imaging apparatus 2A or 2B without being conscious of the width of the imaging apparatus 2.

Figure 26A:
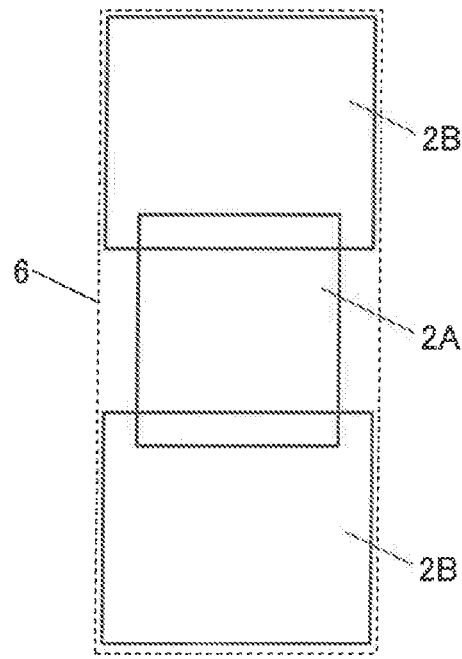
FIG. 26A is a front view of a radiographic imaging apparatus and a grid provided for a radiographic imaging system according to example 13 of the embodiment.

Furthermore, as shown in FIG. 26A, by increasing the width of the grid 6, it is possible to obtain a lengthy image $I_L$ making the most of the size of the imaging apparatus 2B.

Figure 26B:
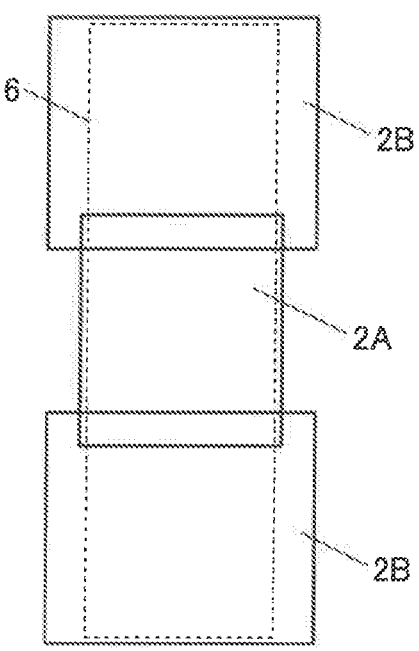
FIG. 26B is a front view of the radiographic imaging apparatus and another grid provided for the radiographic imaging system according to example 13 of the embodiment.

Note that as shown in FIG. 26B, a grid 6 having the same width as that of the imaging apparatus 2A of small width may also be used.

Furthermore, the holder 4 may be configured such that the imaging apparatus 2B of large width sticks out from both sides.

With such a configuration, since the imaging apparatus 2 sticks out from both sides, it is possible to reduce expansion of the cover 45.

Example 13

The plurality of imaging apparatuses 2 loaded into the holder 4 may have different thicknesses. There is no problem if the thickness of the loaded imaging apparatus 2 matches an upper limit of loadable thickness, whereas if the thickness of the loaded imaging apparatus 2 is smaller than the upper limit of thickness, the imaging apparatus 2 is enabled to move in the thickness direction of the imaging apparatus 2 by an amount corresponding to the difference. In that case, for example, the holder 4 may vibrate after a distance (SID) between the focus of radiation and the imaging apparatus 2 is confirmed, imaging may be performed despite the SID being different from a set value, making image combining processing difficult.

In view of such a problem, a biasing member may be provided to bias the imaging apparatus 2 loaded into the holder 4 toward the direction in which the radiation exposure apparatus 1 is located.

Figure 27:
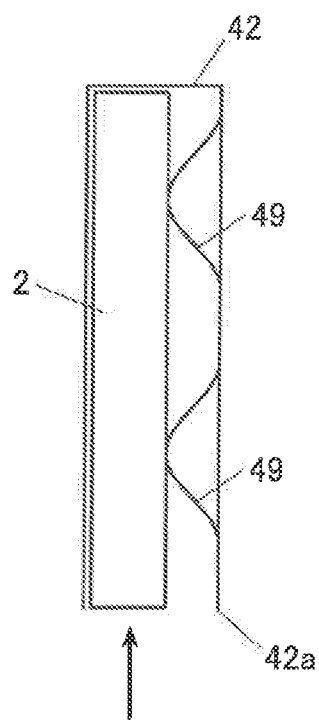
FIG. 27 is a cross-sectional view of the radiographic imaging apparatus and the holder provided for the radiographic imaging system according to example 13 of the embodiment.

More specifically, as shown, for example, in FIG. 27, a curved flat spring 49 is provided on a surface opposite to the rear face of the imaging apparatus 2 in a member that forms the rear face of the holder 4, which is convex toward the direction in which the radiation exposure apparatus 1 is located.

With such a configuration, even when the holder 4 is loaded with the imaging apparatus 2 thinner than an upper limit of thickness loadable into the holder 4, movement in the thickness direction is restricted, making it possible to prevent the SID from changing after confirming the SID.

Note that an inner wall of each loader opposite to the rear face of the imaging apparatus 2 may be configured to be movable in the thickness direction of the imaging apparatus 2 and fixable at any given position, moved so as to be pressed against the imaging apparatus 2 and fixed after loading of the imaging apparatus 2.

Example 14

With the radiographic imaging system 100 according to the above embodiment, it is also possible to load the holder 4 with a smaller number of imaging apparatuses 2 than the number of loadable holders 4 and perform lengthy imaging. The holder 4 can be used for lying imaging as described above. In this case, in lying imaging in which a stage in which the holder 4 is not loaded with the imaging apparatus 2 becomes hollow, if the subject lies on such a holder 4 and a load applies to the holder 4, locations where the imaging apparatus 2 is not loaded cannot support the load, and the holder 4 may deflect or may be damaged.

In view of such a problem, imaging may be performed with a dummy imaging apparatus having the same shape as that of the imaging apparatus 2 and having no function as the imaging apparatus 2 loaded in the stage in which the holder 4 is loaded with no imaging apparatus 2.

With such a configuration, no cavity is generated in the holder 4, and so it is possible to keep strength strong enough to resist the load when the subject lies and prevent deflection or damage from being generated in the holder 4.

Although the present invention has been described based on the embodiment so far, it goes without saying that the present invention is not limited to the above-described embodiment and can be modified as appropriate without departing from the spirit and scope of the present invention.

An example has been disclosed above where an HDD or a semiconductor memory is used as a computer-readable medium for a program according to the present invention, but the present invention is not limited to this example.

As other computer-readable media, it is possible to use a non-volatile memory such as flash memory and a portable recording medium such as a CD-ROM.

Furthermore, as a medium that supplies data of the program according to the present invention via a communication channel, a carrier wave (carrier) is also applicable to the present invention.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese Patent Application No. 2018-009703, filed on 24 Jan. 2018, is incorporated herein by reference in its entirety.

What is claimed is:

1. An image processing apparatus comprising a hardware processor which:
    acquires first image data and second image data which is different from the first image data from among a plurality of pieces of image data generated by a plurality of radiographic imaging apparatuses disposed so as to form a line along an imaging target region of a subject and respectively generating image data of radiographic images by receiving radiation via the imaging target region;
    detects a width in a direction orthogonal to a direction in which a first image based on the first image data acquired and a second image based on the second image data are arranged side by side;
    corrects, when the width of the first image detected is different from the width of the second image, at least one piece of image data of the first image data and the second image data so that the widths of both pieces of image data come closer to each other; and
    combines a plurality of pieces of image data including the image data corrected to thereby generate one piece of lengthy image data.

2. The image processing apparatus according to claim 1, wherein when the detected width of the second image is larger than the width of the first image, the hardware processor corrects the second image data so that when the first image and the second image are arranged side by side, the width of a region in the second image that sticks out in the width direction from the first image is reduced.

3. The image processing apparatus according to claim 2, wherein the hardware processor corrects the second image data so that the width of the region in the second image that sticks out in the width direction from the first image is cut.

4. The image processing apparatus according to claim 1, wherein when the detected width of the second image is smaller than the width of the first image, the hardware processor corrects the second image data so that when the first image and the second image are arranged side by side, at least part of a region where no image exists, generated between an end in the width direction of the second image and an extension line extending from an end in the width direction of the first image toward the direction in which the first and second images are arranged side by side, is interpolated as part of the second image.

5. The image processing apparatus according to claim 4, wherein the hardware processor corrects the second image data so that a whole region where no image exists, generated between the end in the width direction of the second image and the extension line extending from the end in the width direction of the first image toward the direction in which the first and second images are arranged side by side, is interpolated as part of the second image.

6. A radiographic imaging system comprising:
a radiation exposure apparatus that generates radiation;
a plurality of radiographic imaging apparatuses disposed so as to form a line along an imaging target region of a subject for generating image data of radiographic images by receiving radiation; and
the image processing apparatus according to claim 1.

7. The radiographic imaging system according to claim 6, wherein at least one of the plurality of radiographic imaging apparatuses has a width in a direction orthogonal to the direction in which the radiographic imaging apparatuses are arranged side by side and a thickness direction of the one radiographic imaging apparatus, which is different from the widths of the other radiographic imaging apparatuses.

8. The radiographic imaging system according to claim 7, further comprising:
a plurality of loaders that can be loaded with the radiographic imaging apparatus provided so as to form a line; and
a holder, a length in the width direction of the imaging apparatus 2 loaded into the loader of which is smaller than a largest width among the widths of the plurality of radiographic imaging apparatuses.

9. The radiographic imaging system according to claim 8, wherein the length of the loader is equal to a smallest width among the widths of the plurality of radiographic imaging apparatuses.

10. The radiographic imaging system according to claim 8, further comprising a grid provided closer to the radiation exposure apparatus side than the radiographic imaging apparatus for restricting scattered radiation included the radiated radiation from entering the radiographic imaging apparatus.

11. The radiographic imaging system according to claim 10, wherein
the grid comprises a plurality of slits, and
a plane passing through the center in the length direction of the loader and orthogonal to the length direction is disposed on a radiation incident plane of the holder so as to pass through a slit positioned at the center among the plurality of slits.

12. The image processing apparatus according to claim 1, wherein the hardware processor corrects at least one piece of image data so that a dimension of the width of the first image or a dimension of the width of the second image is reduced or increased.

13. The image processing apparatus according to claim 1, wherein the hardware processor corrects the at least one piece of image data of the first image data and the second image data by cutting a larger one of the first image and the second image having a larger width to reduce the width or extrapolating a smaller one of the first image and the second image to increase the width.

14. A radiographic lengthy image imaging method comprising:
arranging a plurality of radiographic imaging apparatuses which generate image data of radiographic images by receiving radiation so as to form a line along an imaging target region of a subject;
capturing radiographic images of the subject;
extracting first image data and second image data which is different from the first image data from among the plurality of pieces of image data generated by the radiographic imaging apparatuses;
measuring a width in a direction orthogonal to a direction in which a first image based on the extracted first image data and a second image based on the second image data are arranged side by side;
correcting, when the measured width of the first image is different from the width of the second image, at least one piece of image data of the first image data and the second image data so that the widths of both pieces of image data come closer to each other; and
combining a plurality of radiographic images including the corrected image data to thereby generate one lengthy image.

15. The radiographic lengthy image imaging method according to claim 14, wherein the plurality of radiographic imaging apparatuses are arranged side by side so that one ends in the width direction are aligned with one another to perform radiation imaging.

16. A non-transitory computer-readable recording medium storing a program for causing a computer to perform:
acquiring first image data and second image data which is different from the first image data from among a plurality of pieces of image data generated by a plurality of radiographic imaging apparatuses disposed so as to form a line along an imaging target region of a subject and generating image data of radiographic images by receiving radiation via the imaging target region;
detecting a width in a direction orthogonal to a direction in which a first image based on the acquired first image data and a second image based on the second image data are arranged side by side;
correcting, when the width of the first image detected is different from the width of the second image, at least one piece of image data of the first image data and the second image data so that the widths of both pieces of image data come closer to each other; and
combining a plurality of pieces of image data including the corrected image data to thereby generate one piece of lengthy image data.

* * * * *